(12) United States Patent
Horn et al.

(10) Patent No.: US 7,789,870 B2
(45) Date of Patent: Sep. 7, 2010

(54) NONWOVEN FABRIC FOR A FEMALE COMPONENT OF A FASTENING SYSTEM

(75) Inventors: Thomas Alexander Horn, Hofheim (DE); Mark James Kline, Okeana, OH (US); Kazuhiko Masuda, Ichihara (JP); Hisashi Morimoto, Ichihara (JP)

(73) Assignee: The Procter & Gamble Company, Cincinnati, OH (US)

( * ) Notice: Subject to any disclaimer, the term of this patent is extended or adjusted under 35 U.S.C. 154(b) by 779 days.

(21) Appl. No.: 11/710,219

(22) Filed: Feb. 23, 2007

(65) Prior Publication Data

US 2008/0208157 A1 Aug. 28, 2008

(51) Int. Cl.
*A61F 13/15* (2006.01)
(52) U.S. Cl. .................. 604/387; 604/391; 604/385.01
(58) Field of Classification Search .......... 604/386–391
See application file for complete search history.

(56) References Cited

U.S. PATENT DOCUMENTS

| | | | |
|---|---|---|---|
| 3,860,003 A | 1/1975 | Buell | |
| 3,911,173 A | 10/1975 | Sprague, Jr. | |
| 3,929,135 A | 12/1975 | Thompson | |
| 4,324,426 A | 4/1982 | Michelson | |
| 4,342,314 A | 8/1982 | Radel et al. | |
| 4,463,045 A | 7/1984 | Ahr et al. | |
| 4,515,595 A | 5/1985 | Kievit et al. | |
| 4,573,986 A | 3/1986 | Minetola et al. | |
| 4,609,518 A | 9/1986 | Curro et al. | |
| 4,610,678 A | 9/1986 | Weisman et al. | |
| 4,629,643 A | 12/1986 | Curro et al. | |
| 4,673,402 A | 6/1987 | Weisman et al. | |
| 4,695,278 A | 9/1987 | Lawson | |
| 4,785,996 A | 11/1988 | Ziecker et al. | |
| 4,834,735 A | 5/1989 | Alemany et al. | |
| 4,842,666 A | 6/1989 | Werenicz | |
| 4,888,231 A | 12/1989 | Angstadt | |
| 4,892,536 A | 1/1990 | Desmarais et al. | |
| 4,909,803 A | 3/1990 | Aziz et al. | |

(Continued)

FOREIGN PATENT DOCUMENTS

EP 1 279 348 A1 1/2003

(Continued)

OTHER PUBLICATIONS

International Search Report.

*Primary Examiner*—Michele Kidwell
(74) *Attorney, Agent, or Firm*—Laura L. Whitmer

(57) ABSTRACT

A fastening system includes an engaging component and a receiving component. The engaging component has a plurality of engaging elements capable of engaging the receiving component. The receiving component includes a nonwoven fabric having composite fibers, an embossed section, and a non-embossed section. The composite fibers are bonded together in the embossed sections. The composite fibers include a first propylene polymer and a second propylene polymer, wherein the first and second propylene polymers extend continually in a longitudinal direction and are arranged such that the second propylene polymer is associated with the first propylene polymer such that the composite fiber forms a crimp therein. The embossed sections have a plurality of zigzag unit patterns arranged in a machine direction which have a ratio of $W_1/W_2$ in the range of about 0.5 to about 2.0.

19 Claims, 12 Drawing Sheets

U.S. PATENT DOCUMENTS

| | | | |
|---|---|---|---|
| 4,940,464 A | 7/1990 | Van Gompel et al. | |
| 4,968,312 A | 11/1990 | Khan | |
| 4,990,147 A | 2/1991 | Freeland | |
| 5,006,394 A | 4/1991 | Baird | |
| 5,037,416 A | 8/1991 | Allen et al. | |
| 5,062,840 A | 11/1991 | Holt et al. | |
| 5,092,861 A | 3/1992 | Nomura et al. | |
| 5,137,537 A | 8/1992 | Herron et al. | |
| 5,147,345 A | 9/1992 | Young et al. | |
| 5,151,092 A | 9/1992 | Buell et al. | |
| 5,171,236 A | 12/1992 | Dreier et al. | |
| 5,221,274 A | 6/1993 | Buell et al. | |
| 5,246,433 A | 9/1993 | Hasse et al. | |
| 5,260,345 A | 11/1993 | Desmarais et al. | |
| 5,269,755 A | 12/1993 | Bodicky | |
| 5,269,775 A | 12/1993 | Freeland et al. | |
| 5,306,266 A | 4/1994 | Freeland | |
| 5,342,338 A | 8/1994 | Roe | |
| 5,387,207 A | 2/1995 | Dyer et al. | |
| 5,397,318 A | 3/1995 | Dreier | |
| 5,460,622 A | 10/1995 | Dragoo et al. | |
| 5,514,121 A | 5/1996 | Roe et al. | |
| 5,518,801 A | 5/1996 | Chappell et al. | |
| 5,540,671 A | 7/1996 | Dreier | |
| 5,554,142 A | 9/1996 | Dreier et al. | |
| 5,569,234 A | 10/1996 | Buell et al. | |
| 5,571,096 A | 11/1996 | Dobrin et al. | |
| 5,607,760 A | 3/1997 | Roe | |
| 5,609,587 A | 3/1997 | Roe | |
| 5,625,222 A | 4/1997 | Yoneda et al. | |
| 5,635,191 A | 6/1997 | Roe et al. | |
| 5,643,588 A | 7/1997 | Roe et al. | |
| 5,653,703 A | 8/1997 | Roe et al. | |
| 5,865,823 A | 2/1999 | Curro | |
| 5,897,545 A | 4/1999 | Kline et al. | |
| 5,938,648 A | 8/1999 | Lavon et al. | |
| 5,941,864 A | 8/1999 | Roe | |
| 5,957,908 A | 9/1999 | Kline et al. | |
| 5,968,025 A | 10/1999 | Roe et al. | |
| 5,977,430 A | 11/1999 | Roe et al. | |
| 5,997,520 A | 12/1999 | Ahr et al. | |
| 6,013,063 A | 1/2000 | Roe et al. | |
| 6,054,202 A * | 4/2000 | Takeuchi et al. | 428/167 |
| 6,120,487 A | 9/2000 | Ashton | |
| 6,120,489 A | 9/2000 | Johnson et al. | |
| 6,168,584 B1 | 1/2001 | Allen et al. | |
| 6,680,422 B2 | 1/2004 | Roe | |
| 6,716,441 B1 | 4/2004 | Osborne et al. | |
| 2002/0019206 A1 | 2/2002 | Deka et al. | |
| 2003/0176132 A1* | 9/2003 | Moriyasu et al. | 442/361 |
| 2003/0233082 A1 | 12/2003 | Kline et al. | |
| 2004/0067709 A1* | 4/2004 | Kishine et al. | 442/327 |
| 2005/0009173 A1 | 1/2005 | Amand | |
| 2007/0007267 A1 | 1/2007 | Rayl et al. | |

FOREIGN PATENT DOCUMENTS

| | | |
|---|---|---|
| WO | 0 381 087 A1 | 8/1990 |
| WO | WO-94/14395 A1 | 7/1994 |
| WO | WO-95/16746 A1 | 6/1995 |
| WO | WO-95/24173 A2 | 9/1995 |
| WO | WO-99/14046 A1 | 3/1999 |

\* cited by examiner

NONWOVEN FABRIC FOR A FEMALE COMPONENT OF A FASTENING SYSTEM

FIELD OF THE INVENTION

The present invention pertains to a nonwoven fabric for the female component of mechanical fasteners with the fiber loops that engage a male component having fastening hooks and which fastens detachably, and to the use of same. The invention further pertains to a nonwoven fabric for the female component of a mechanical fastener utilizing a nonwoven fabric with a fiber thermally compressed by a heat-embossing finish and use of same.

This invention was made pursuant to a joint research agreement between The Procter & Gamble Company and Mitsui Chemicals Inc.

BACKGROUND OF THE INVENTION

Mechanical fasteners where a male component provided with fastening hooks and a female component provided with fiber loops are engaged and fastened detachably can be used for disposable products such as disposable diapers. The use of these mechanical fasteners can facilitate removal of the disposable diaper and can provide appropriate fastening strength. Typically, the mechanical fastener comprises an engaging component and a female component. In some instances, the female component may comprise a nonwoven fabric.

Nonwoven fabrics provided with loops formed by entanglement of fibers based on needle punching, a heat-embossing finish, etc., have been proposed for the female component of the aforementioned mechanical fasteners. Traditionally, nonwoven fabrics have been formed into webs by means of needle punching, stitch bonding, and water-jet interweaving. Additionally, nonwoven fabrics can be formed into webs by thermally compressing the fibers by means of a heat-embossing finishing such loops are formed in the non-embossed sections between the thermally compressed, embossed sections. Also, a nonwoven fabric for use as the female component of a fastener can be formed where intermittent non-embossed sections are formed between continuous embossed sections.

It is important for the female component to have sufficient adhesive strength. For example, having a sufficient adhesive strength with the male component can reduce the likelihood of a peel strength reduction despite repeated fastening and unfastening with the male component. Furthermore, it is important to have sufficient mechanical strength in both the MD direction and CD direction. Also, in order to be used as a fastening component for articles that come in direct contact with the skin such as disposable diapers, incontinence products, and surgical wear, high bulkiness and a soft feel to the touch are desirable.

Typically, the primary purpose of the nonwoven fabric for use as the female component of a fastening system, is to increase the peel strength and prevent a reduction of the peel strength after repeated use. However, the nonwoven fabric for the female component of a fastening system having sufficient adhesive strength in all areas of peel strength, repeated peel strength and tension shear strength, and at the same time, having high mechanical strength in both the MD direction and CD direction as well as high bulkiness has not been known in the past.

Therefore a need exists for a nonwoven fabric having high bulkiness, and excellent softness and a nonwoven fabric laminate provided with water repellency and surface smoothness, along with adhesive strength and mechanical strength when used as the female component of the fastening system.

SUMMARY OF THE INVENTION

The purpose of the present invention is to provide a fastening system having a nonwoven fabric for use as the female component of a fastener having sufficient adhesive strength in all areas of peel strength, repeat peel strength, and tension shear strength, and at the same time, having high mechanical strength in both of MD direction and CD direction as well as high bulkiness.

A fastening system constructed in accordance with the present invention may comprise an engaging component and a receiving component. The engaging component comprises a plurality of engaging elements capable of engaging the receiving component.

The receiving component comprises a nonwoven fabric having composite fibers, embossed sections and nonembossed sections. The composite fibers are bonded to each other in the embossed sections. Additionally, the composite fibers comprise a first propylene polymer and a second propylene polymer, wherein the first and second propylene polymers extend continually in a longitudinal direction, and the second propylene type polymer is associated with the first propylene type polymer such that the composite fiber forms a crimp therein. The composite fibers are bonded together in the embossed sections, and wherein the unit pattern has a ratio of $W_1/W_2$ in the range of about 0.5 to about 2.0.

In some embodiments, the embossed sections comprise a plurality of zigzag unit patterns arranged in a machine direction with predetermined spacings. The zigzag unit patterns continually extend generally parallel with a cross direction of the embossing roll. The zigzag unit patterns each comprise a continual zigzag pattern in which a plurality of first diagonal lines and a plurality of second diagonal lines are arranged alternately and are connected together adjacent to end parts of the diagonal lines. The first diagonal lines are arranged at a first angle with respect to the cross direction and are inclined to one side at about the same first angle relative to the machine direction. The second diagonal lines are arranged at a second angle with respect to the cross direction and being inclined to the other side at about the same second angle relative to the machine direction. The first diagonal lines and the second diagonal lines in the zigzag unit pattern form triangles comprising three adjacent contact points of diagonal lines. The triangles include part of the zigzag unit pattern extending in the machine direction adjacent thereto.

In some embodiments, a disposable article may comprise the fastening system described above. The article may comprise an outer-facing surface and a wearer-facing surface. The fastening system can be disposed on the wearer-facing surface or the outer-facing surface of the disposable article.

DETAILED DESCRIPTION OF THE INVENTION

Figure 1A:
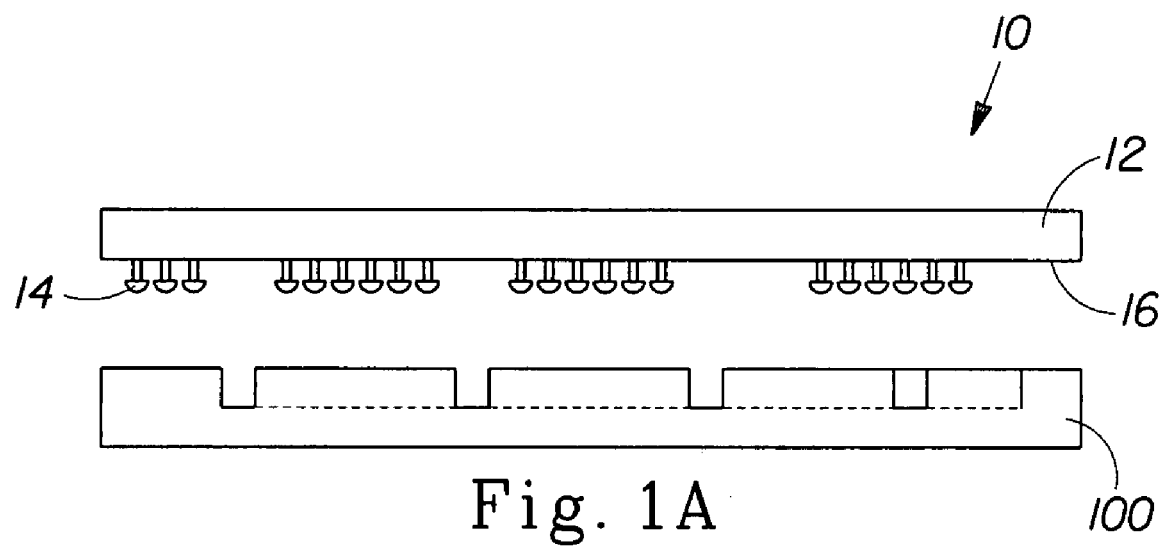
FIG. 1A is an elevation view showing a fastening system constructed in accordance with the present invention.

Definitions:

As used herein, the terms "absorbent article" and "article" refer to a wearable device that absorbs and/or contains liquid and, more specifically, refers to a device that is placed against or in proximity to the body of the wearer to absorb and contain the various exudates discharged from the body. Suitable examples include diapers, training pants, refastenable pants, pull-on garments, adult incontinence products and feminine care products such as sanitary napkins. Furthermore, the terms "absorbent article" and "article" include a "disposable absorbent article" which is intended to be discarded and not laundered or otherwise restored after no more than ten uses, preferably after no more than five uses, and most preferably after a single use (although certain components may be recycled, reused, or composted).

As used herein, the term "adhesive strength" includes "peel strength", "repeat peel strength" and "shear strength". Additionally, "shear strength" is sometimes referred to herein as "tension sheer strength" or "tension strength".

"Body-facing", "wearer-facing", "outer-facing", and "garment-facing", refer respectively to the relative location of an element or a surface of an element or group of elements. "Body-facing" and "wearer facing" imply the element or surface is nearer to the wearer during wear than some other element or surface. "Garment-facing" and "outer facing" imply the element or surface is more remote from the wearer during wear than some other element or surface (i.e., element or surface is proximate to the wearer's garments that may be worn over the disposable absorbent article).

As used herein, the term "crimp" refers to a characteristic of a fiber having at least one fold or ridge. The term "crimp" includes fibers which have multiple folds, fibers which have curls, and/or fibers which form a spiral or helical structure.

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

As used herein "elastically extensible" refers to characteristics of extensible materials that have the ability to return to approximately their original dimensions after a force that extended the extensible material is removed. Herein, any material or element described as "extensible" may also be "elastically extensible" unless otherwise provided.

As used herein the term "joined" encompasses configurations whereby an element is directly secured to another element by affixing the element directly to the other element, and configurations whereby an element is indirectly secured to another element by affixing the element to an intermediate member(s) which in turn are affixed to the other element.

The term "longitudinal" is used herein to refer to a direction which is generally parallel to the longest edge of an element except where otherwise noted. In the context of disposable absorbent articles, a "longitudinal" direction runs substantially perpendicular from a waist edge to an opposing waist edge of the article and generally parallel to the maximum linear dimension of the article. Directions within ±45 degrees of the longitudinal direction are considered to be "longitudinal".

The term "lateral" refers to a direction running generally perpendicular to and in the same plane as the "longitudinal" direction. In the context of disposable absorbent articles, a "lateral" direction runs from one longitudinal edge of the article to an opposing longitudinal edge of the article. Directions within ±45 degrees of the lateral direction are considered to be "lateral".

The terms "machine direction" or "MD" refer to a direction which is generally parallel to the forward direction of a material, member, element, item, component, etc. through a process. For example, nonwovens are typically formed with a machine direction that corresponds to the long or rolled direction of fabrication. The machine direction can also be the primary direction of fiber orientation in the nonwoven.

The terms "cross machine direction" or "CD" refer to a direction which is generally perpendicular to and in the same plane as the machine direction.

The terms "pant", "training pant", "closed diaper", "prefastened diaper", and "pull-on diaper", as used herein, refer to disposable garments having a waist opening and leg openings designed for infant or adult wearers. A pant can be configured such that the pant has a closed waist and leg openings prior to being donned on the wearer, or the pant can be configured such that the waist is closed and the leg openings formed while on the wearer. A pant may be preformed by any suitable technique including, but not limited to, joining together portions of the article using a refastenable fastening system. A pant may be preformed anywhere along the circumference of the article (e.g., side fastened, front waist fastened, rear waist fastened). Examples of suitable pants are disclosed in U.S. Pat. No. 5,246,433; U.S. Pat. No. 5,569,234; U.S. Pat. No. 6,120,487; U.S. Pat. No. 6,120,489; U.S. Pat. No. 4,940,464; U.S. Pat. No. 5,092,861; U.S. Pat. No. 5,897,545; U.S. Pat. No. 5,957,908; and U.S. Patent Publication No. 2003/0233082 A1.

As used herein, the term "receiving component" is sometimes referred to herein as "female fastener component".

Description:

The fastening system of the present invention comprises a female fastener component having a sufficient adhesive strength in all areas of peel strength, repeat peel strength, and tension shear strength as well as high mechanical strength in both of MD direction and CD direction. Furthermore, the nonwoven fabric for use as the female fastener component of the present invention has high bulkiness and softness and can be used effectively for disposable absorbent articles or many other consumer goods as discussed hereafter.

As shown in FIG. 1A, a fastening system 10 constructed in accordance with the present invention may comprise an engaging component 12 and a receiving component 100. The engaging component 12 may comprise a plurality of engaging elements 14 which extend outward from an engaging surface 16. The receiving component 100 may comprise a plurality of looped fibers (not shown) which are capable of becoming entangled with the plurality of hooks 14 of the engaging component 12. Examples of suitable engaging components are discussed hereafter.

The fastening system 10 can be utilized in a variety of consumer and commercial goods which may benefit from having the fastening system of the present invention. Some examples of articles which can utilize the fastening system of the present invention include disposable absorbent articles, body wraps, packaging, and industrial connections for abrasive pads, medical products, and the like.

Figure 15A:
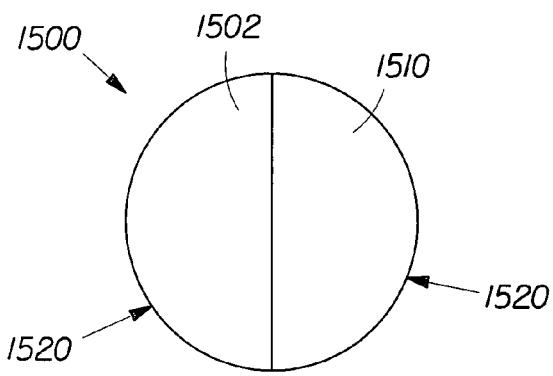
FIGS. 15A-15D are cross sectional views showing bi-component fibers.

The receiving component 100 may comprise a nonwoven fabric. The nonwoven fabric for use as the receiving component of the present invention may comprise a nonwoven fabric made of a crimped composite fiber (hereinafter simply referred to as composite fiber or a nonwoven fabric laminate made with same). The crimped composite fiber may comprise a first propylene type polymer and a second propylene type polymer. The first and second propylene type polymers can be arranged to occupy substantially separate areas at the cross sections of the composite fibers and extend continuously in the length direction. In some embodiments, each of the first and second propylene type polymers form at least a part of the peripheral surface along the length direction of the composite fiber. In some embodiments, as shown in FIG. 15A, a composite fiber 1500 can be a side-by-side type composite fiber where a first propylene type polymer 1502 and a second propylene type polymer 1510 extend side-by-side in the length direction of the composite fiber such that the first and the second propylene type polymers 1502 and 1510 each form about 50% of a peripheral surface 1520 of the composite fiber 1500.

Figure 15B:
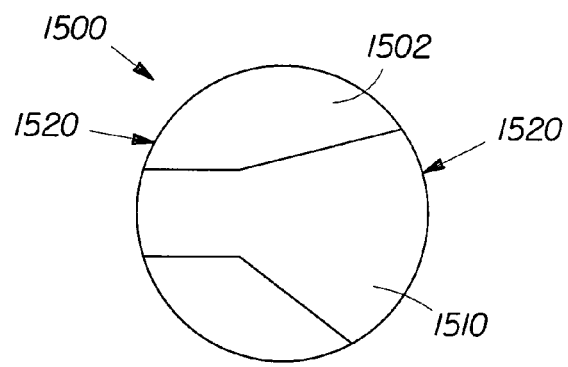
Figure 15C:
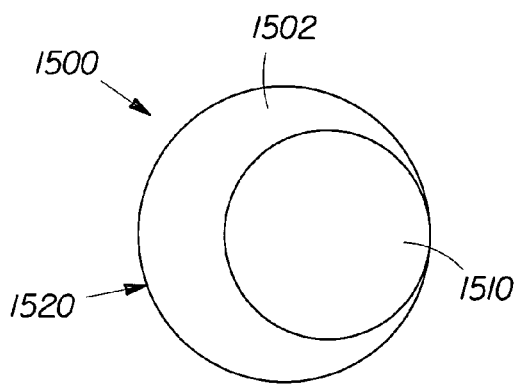
Figure 15D:
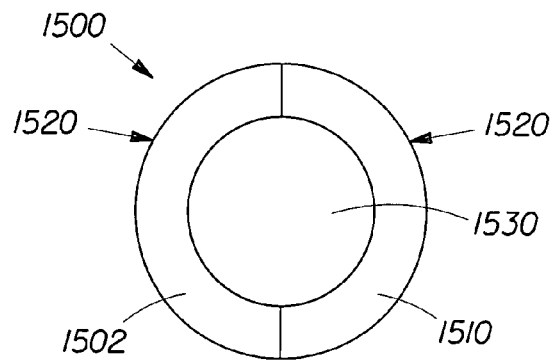

The first propylene type polymer 1502 and the second propylene type polymer 1510 can be arranged in any suitable configuration which would yield a crimp in the resulting fiber 1500. For example, in some embodiments, as shown in FIG. 15B, the second propylene type polymer 1510 may form a cross like pattern within the first propylene type polymer 1502 which is asymmetrically distributed within the first propylene type polymer. In some embodiments, as shown in FIG. 15C, the second propylene type polymer 1510 can be completely surrounded by the first propylene type polymer 1502 such that the first propylene polymer 1502 comprises about 100% of the peripheral surface 1520 of the composite fiber 1500. The second propylene type polymer 1510 can be distributed within the first propylene type polymer 1502 asymmetrically such that a crimp results in the resulting fiber 1500. In some embodiments, as shown in FIG. 15D, the first propylene type polymer 1502 and the second propylene type polymer 1510 may be in a side-by side orientation such that an opening 1530 is formed between the first propylene type polymer and the second propylene type polymer.

Additionally, embodiments are contemplated where the second propylene type polymer 1510 comprises any number greater than about 50% of the peripheral surface 1520 of the composite fiber 1500. Additionally, embodiments are contemplated where the second propylene type polymer 1510 comprises any number less than about 50% of the peripheral surface 1520 of the composite fiber 1500. Also, the first propylene type polymer 1502 can be configured similarly to the second propylene type polymer 1510 and vice versa. Embodiments are contemplated where fibers are crimped such that they curl or form spiral structures.

In some embodiments, the melting point of the first propylene type polymer 1502 measured by differential scanning calorimetry (DSC) can be at least 15° C. higher than the melting point of the second propylene type polymer 1510. In some embodiments, the melting point of the first propylene type polymer 1502 can be in a range of about 15 degrees C. to about 60 degrees C., or any number within the range, higher than the melting point of the second propylene type polymer 1510.

Furthermore, the measured weight ratio of the first propylene type polymer 1502 to the second propylene type polymer 1510 can be, in some embodiments, in the range of about 50/50 to about 5/95 or any ratio within the range. In some embodiments, the weight ratio can be in the range of about 40/60 to about 10/90 or any ratio within the range. In some embodiments, the weight ratio can be in the range of about 30/70 to about 10/90 or any ratio within the range.

In some embodiments, a possible method for determining the weight ratio of the first propylene type polymer 1502 to the second propylene type polymer 1510 may be Temperature Rising Elution Fractionation (TREF). For example, using a Cross Fractionation Chromatograph T-150A manufactured by Mitsubishi Chemicals Corporation; an IR spectrometer 1 ACVF 3.42 micrometer at 135 degrees C., manufactured by Miran; and a TREF column having an inner diameter of 4 mm and a length of 150 mm, the weight ratios may be determined.

Other steps may include, utilizing an eluent of o-dichlorobenzene (ODCB) at a flow rate of 1.0 mL/min, a concentration of sample of 30 mg/10 mL-ODCB, and a sample volume of 500 micro liters. Yet other conditions may include cooling the sample from 135 degrees C. to 0 degrees C. in 135 minutes and then holding the sample at 0 degrees C. for 60 minutes. Fractionation steps may include 0, 20, 40, 50, 60, 75, 80, 83, 86, 89, 92, 95, 98, 101, 104, 106, 108, 110, 112, 114, 116, 118, 120, 122, 125, 130, and 135 degrees C.

A resulting elution curve can be divided by a perpendicular line (perpendicular to the x-axis) at a valley between two peaks. The perpendicular line can create a first portion and a second portion of the elution curve. The first portion may comprise the area under the curve to the right of the perpendicular line while the second portion may comprise the area under the curve to the left of the perpendicular line. The weight ratio of the first propylene type polymer relative to the second propylene type polymer may be calculated by a ratio first portion to the second portion.

In some embodiments, the melt-flow rate of the first and second propylene type polymers measured according to the specification of ASTM D1238 (MFR: measuring temperature 230° C., load 2.16 kg) (second propylene type polymer/first propylene type polymer) can be in the range of about 0.8 to about 1.2 or any individual number within the range. In some embodiments, the melt-flow rate can be in the range of about 0.9 to about 1.1.

In some embodiments, the area ratio of the first propylene type polymer and the second propylene type polymer at the cross section of the composite fiber can be about the same as the weight ratio. For example, in some embodiments, a ratio of the cross sectional area of the first propylene type polymer to the cross sectional area of the second propylene type polymer can be in a range of about 50/50 to about 5/95 or any ratio within the range. In some embodiments, the ratio can be in the range of about 40/60 to about 10/90 or any ratio within the range. In some embodiments, the ratio can be in the range of about 30/70 to about 10/90 or any ratio within the range.

When the aforementioned condition is satisfied, a crimped state can be achieved in the composite fiber. A suitable number of crimps according to the specification of JIS L1015 can be in the range of about 5 crimps to about 50 crimps/25 mm or any individual number within the range.

In the present invention, measurement of the melting point of the first and second propylene type polymers based on DSC was done by an instrument of the Perkin Elmer Corp. As the sample was set on a measuring plate, the temperature was increased from 30° C. to 200° C. at a temperature increase rate of 10° C./min; 200° C. was retained for 10 min; then, the temperature was reduced to 30° C. at a temperature decrease rate of 10° C./min; then, the temperature was again increased from 30° C. to 200° C. at a temperature increase rate of 10° C./min and measurements were made on the second run.

Furthermore, it is desirable when two or more melting point peaks in the composite fiber exist based on DSC and the area of the lowest melting point peak is greater than the area of the higher melting point peak. The measurement of the melting point of the composite fiber based on DSC was done by the aforementioned device with the sample set on the measuring plate as the temperature was increased from 30° C. to 200° C. at a temperature increase rate of 10° C./min, and the aforementioned measurement was made during the first run. In the aforementioned measurement method, the melting point is obtained as the peak on the endothermic curve and the area of the melting point peak can be obtained along with the value of the melting point. When two melting point peaks of the composite fiber obtained by the measuring method of the first run overlap, the peak with an absence of other peaks is estimated according to the shape of the peak with maximum strength, and the area is obtained and comparison is made with the area of the other peaks.

In regard to the first and second propylene type polymer comprising the composite fiber of the present invention, propylene homopolymer and copolymers of propylene and one or more different types of α-olefins with 2-20 carbon atoms, preferably, 2-8 carbon atoms such as ethylene, 1-butene, 1-pentene, 1-hexene, 1-octene and 4-methyl-1-pentene, and having propylene as the primary structural unit can be utilized in some embodiments. Among those listed above, a propylene homopolymer or propylene-ethylene random copolymer having an ethylene unit content in the range of about 0 to about 10 mol % and MFR in the range of about 20 to about 200 g/10 min is desirable.

In some embodiments, the first propylene type polymer can be a propylene homopolymer and the second propylene type polymer can be a random copolymer of propylene and a small amount of ethylene having a uniform ethylene component content in the range of about 10 mol % or below, and preferably in the range of about 2 to about 10 mol %, from the standpoint of production of a nonwoven fabric having excellent fastening strength and mechanical strength as well as high bulkiness and softness suitable for use as the female component of a fastening system. In this case, the amount of ethylene unit component is obtained according to a standard method using $^{13}$C-NMR spectral analysis.

In some embodiments, the melting point of the first propylene type polymer can be in the range of about 120 to about 175° C., or any individual number within the range. In some embodiments, the melting point of the second propylene type polymer can be in the range of about 110 to about 155° C. The aforementioned propylene type polymers can be produced utilizing a high stereospecific polymeric catalyst.

In addition to propylene type polymers, an appropriate amount of other components may be included in the aforementioned composite fiber, as needed, as long as the purpose of the present invention is not lost. Some examples of suitable other components may include: heat stabilizers, weather resistance agents, a variety of stabilizers, antistatic agents, slip agents, anti-blocking agents, antifoggants, lubricants, dyes, pigments, natural oils, synthetic oils, waxes, etc. Some suitable examples of stabilizers include, antioxidants such as 2,6-di-t-butyl-4-methylphenol (BHT); phenolic antioxidants such as tetrakis[methylene-3-(3,5-di-t-butyl-4-hydroxyphenyl) propionate]methane, β-(3,5-di-t-butyl-4-hydroxyphenyl) alkyl ester propionate, and 2,2'-oxamidebis[ethyl-3-(3,5-di-t-butyl-4-hydroxyphenyl) propionate; fatty acid metal salts such as zinc stearate, calcium stearate, and calcium 1,2-hydroxystearate; polyhydric alcohol fatty acid esters such as glycidyl monostearate, glycidyl distearate, pentaerythritol monostearate, pentaerythritol distearate and pentaerythritol tristearate, etc. Furthermore, one or more different types of the components may be mixed and used in combination as well. Some examples of suitable lubricants include oleic acid amide, erucic acid amide, stearic acid amide, etc.

Furthermore, in some embodiments, the composite fiber may further include fillers such as silica, diatomaceous earth, alumina, titanium oxide, magnesium oxide, pumice powder, pumice balloon, aluminum hydroxide, magnesium hydroxide, basic magnesium carbonate, dolomite, calcium sulfate, potassium titanate, barium sulfate, calcium sulfite, talc, clay, mica, asbestos, calcium silicate, montmorillonite, bentonite, graphite, aluminum powder, and molybdenum sulfide.

Mixing of propylene type polymer and the optional components mentioned above can be achieved using any suitable conventional method.

A nonwoven fabric provided with an embossed section having a specific pattern described below utilizing the aforementioned composite fiber has very high adhesive strength and high mechanical strength when used as a female component of the fastener. Furthermore, the aforementioned nonwoven fabric has high bulkiness as well as excellent softness. Also, the aforementioned composite fiber has excellent spinnability and excellent anti-flocking property. Therefore, high productivity can be achieved, and in particular, flocking can be controlled at the time of embossing finish, and high-speed processing can be made possible.

The nonwoven fabric comprising the crimped composite fiber does not require a special device, and a standard composite hot-melt spinning method can be used. In some embodiments, a spun-bonded nonwoven fabric produced by spun-bonding method with high productivity is especially desirable.

Production of a spun-bonded nonwoven fabric can be achieved, in some embodiments, when the first propylene type polymer that forms one area of the composite fiber and the second propylene type polymer that forms the other area are melted by a separate extruder. The first propylene type polymer and the second propylene type polymer can be extruded from a nozzle plate having a composite spinning nozzle structure in such a manner that each molten material can be extruded while forming a desired fiber structure so as to extrude a composite long fiber. The long fiber extruded can be chilled by cooling air. In some embodiments, tension is applied with blowing air to form a predetermined fiber size. The fiber can be collected as is on a collection belt to deposit to form a predetermined thickness, and for bonding treatment, thermal fusion can be applied to the nonwoven fabric using embossing finish. The fiber size of the nonwoven fabric is preferably in the range of about 0.5 to about 5.0 denier, or any individual number within the range. In some embodiments, the fiber size can be in the range of about 1.0 to about 4.0 denier. The basis weight of the nonwoven fabric, in some embodiments, can be in the range of about 20 to about 80 $g/m^2$, or any individual number within the range. In some embodiments, the basis weight can be in the range of about 30 to about 60 $g/m^2$.

The embossing finish can be achieved using a standard embossing roll. For example, an engraved roll corresponding to the emboss pattern can be used for at least one of a pair of rolls. A nonwoven fabric can be passed between the rolls and thermal compression can be applied. In accordance with the above mentioned properties, etc., required for the nonwoven fabric produced, temperature, contact pressure, etc., of the rolls can be adjusted for the degree of the thermal compression.

Figure 1B:
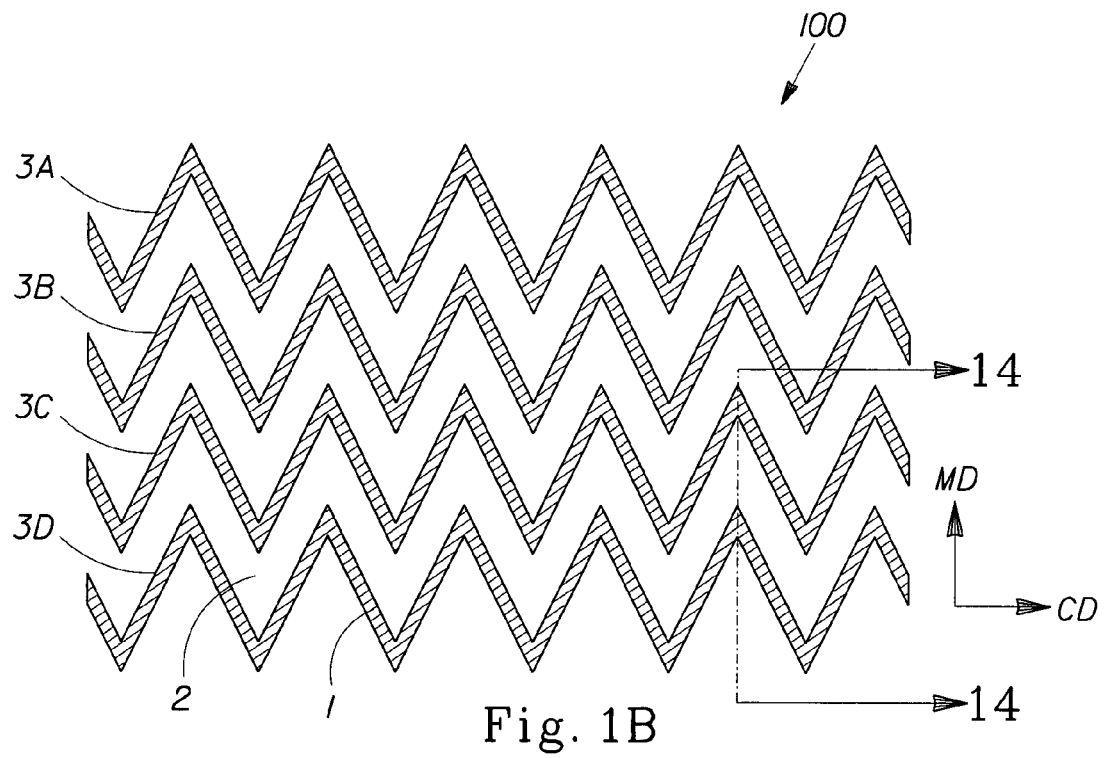
FIG. 1B is a partial top view of an application example of the nonwoven fabric for use as the female component of the fastener of the present invention.
Figure 2:
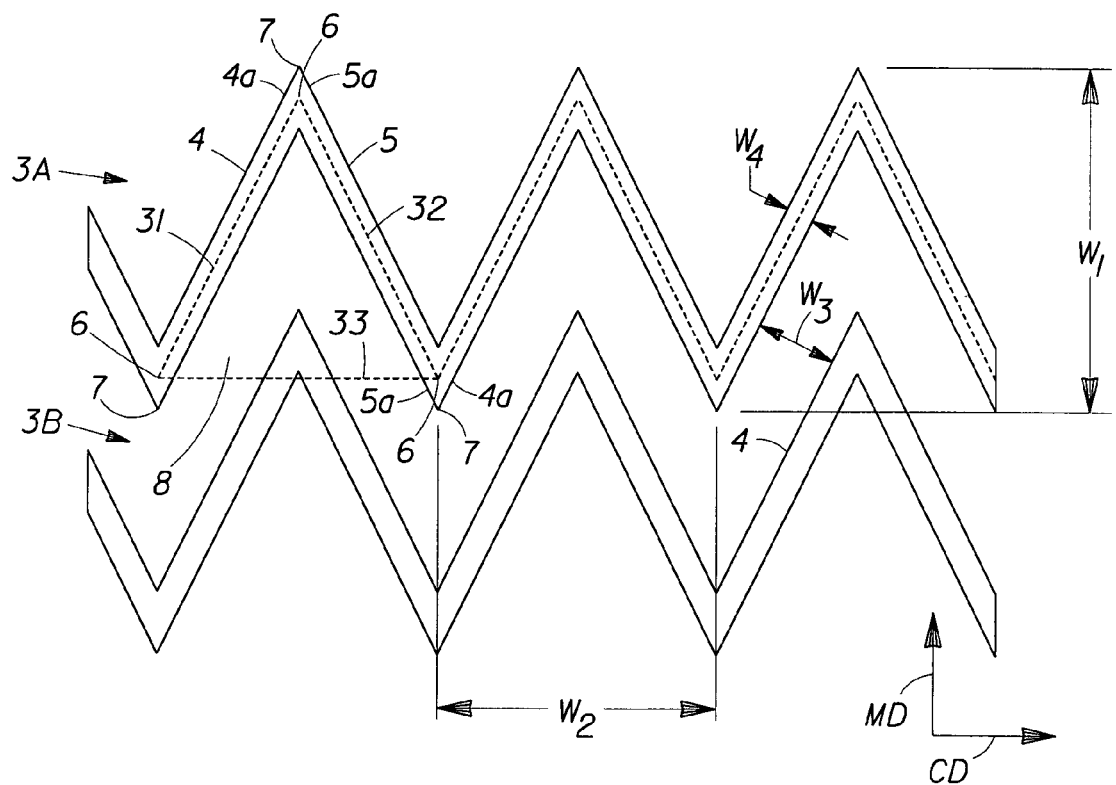
FIG. 2 is an enlarged partial view of the nonwoven fabric for use as the female component of the fastener of FIG. 1B.

The embossed pattern of the nonwoven fabric for use as the female component of the fastening system of the present invention is explained below. As shown in FIG. 1B a partial top view of an application example of the nonwoven fabric for use as the female component of the fastener of the present invention, and FIG. 2 is an enlarged view of the nonwoven fabric of FIG. 1B.

In FIG. 1B, embossed sections 1, shown by the shaded area correspond to the area where the crimped composite fiber is thermally compressed by embossing rolls. Nonembossed sections 2, correspond to the area between embossed sections 1, and represent the area where thermal compression is not applied to the crimped composite fiber. In the nonembossed sections 2, the crimped composite fiber forms loops that undergo an engagement with the hook member of the male component during fastening of the fastening system.

Figure 14:
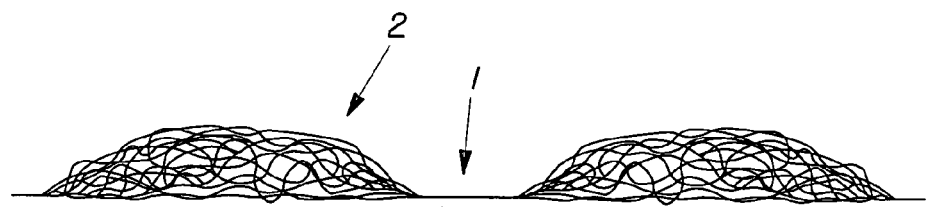
FIG. 14 is a vertical cross sectional view of the nonwoven fabric for use as the female component of the fastener of an application example of the present invention.

As shown in FIG. 14, the cross section of the nonwoven fabric for use as the female component of a fastener shows recessed embossed section 1 and the nonembossed section 2. In some embodiments, the difference in height between the non-embossed section 2 and embossed section 1 can be in the range of about 0.1 to about 2 mm. The shape of the cross section of the raised area of the engrave of the embossing roll used for formation of embossed section 1 is not especially limited, and any suitable shape, trapizoidal, for example, can be used.

As shown in FIG. 1B, in some embodiments, embossed section 1 in the nonwoven fabric may comprise an embossed pattern where continuous zigzag unit patterns 3A, 3B, 3C, and 3D, are arranged in an MD direction (Machine Direction) at predetermined intervals substantially parallel to a CD direction (Cross Machine Direction) of the embossing roll. Embodiments comprising more than four zigzag unit patterns and less than four zigzag unit patterns are contemplated.

As shown in FIG. 2, in some embodiments, a plurality of unit patterns 3A and 3B may each comprise a zigzag pattern where many first shaded areas 4 slanted at an angle to the CD direction and slanted toward one side at about the same angle with respect to the MD direction and many second shaded areas 5 slanted at an angle to the CD direction and slanted toward the other side in the MD direction at about the same angle can be arranged alternately. As shown, in some embodiments, the first shaded areas 4 and the second shaded areas 5 can mutually connect adjacent end member 4a of the first shaded area 4 and adjacent end member 5a of the second shaded area 5.

As shown, in some embodiments, the first shaded areas 4 and the second shaded areas 5 may intersect such that no portion of the first shaded area 4 and no portion of the second shaded area 5 extend beyond the shaded area with which it intersects. A contact point 6 between the first shaded area 4 and the second shaded area 5 can exist. Referring to unit pattern 3A, for example, the contact point 6 is defined as the outermost point of the intersection between a first centerline 31 and a second centerline 32. The first centerline 31 can be disposed in the first shaded area 4, and the second centerline 32 can be disposed in the second shaded area 5. Each of the first shaded areas 4 and second shaded areas 5 may comprise a centerline. Note that the term "outermost" is taken with respect to the unit pattern for which the contact points are trying to be determined.

An apex 7 can be spatially displaced away from the contact points. Again referring to unit pattern 3A, the apex 7 is defined as the outermost point of either first shaded area 4 or the second shaded area 5 which ever comprises the outermost point of the unit pattern being referenced.

As shown, a portion of an adjacent unit pattern, e.g. 3B can be enclosed inside a triangle 8 formed by three adjacent contact points 6 of the first shaded area 4 and the second shaded area 5 of the unit pattern 3A. For example, the first centerline 31 of the first shaded area 4 can form one leg of the triangle 8. Another leg of the triangle 8 can be formed by the second centerline 32 of the second shaded area 5. A base 33 of the triangle 8 can be a line, which is generally parallel to the CD direction, between two contact points 6 which are spaced apart laterally.

A unit pattern can have a width $W_1$ and a width $W_2$. The width $W_1$ can be defined as the maximum linear distance, which is generally parallel to the MD direction, between the apexes 7 of a shaded area. For example, as shown, the width $W_1$ can be the distance between the apexes 7 of the second shaded area 5. The width $W_2$ can be defined as the maximum linear distance between the contact point 6 of a first shaded area 4 and a second shaded area 5 and the contact point 6 of the first shaded area 4 and another second shaded area 5. The distance $W_2$ is generally parallel to the CD direction. One skilled in the art can recognize that the distance $W_2$ can correspond to the period of the unit pattern in some embodiments.

In some embodiments, a ratio of $W_1/W_2$ can be in the range of about 0.1 to about 10, or any individual number within the range. In some embodiments, the ratio can be in the range of about 0.5 to about 2.0. In some embodiments, the width $W_1$ can be in the range of about 3 to about 50 mm or any individual number within the range. In some embodiments, the width $W_1$ can be in the range of about 5 to about 20 mm.

When each of the aforementioned conditions is satisfied, a female fastener component can be produced having sufficient adhesive strength in all areas of peel strength, repeat peel strength, and tension shear strength as well as high mechanical strength in both the MD direction and CD direction. In particular, it is desirable for the female component of the fastener to have high repeat peel strength and high mechanical strength in the CD direction, and overlapping of adjacent unit patterns 3A and 3B in the MD direction such that a part of the unit pattern 3B is disposed inside the triangle 8 formed by the three adjacent contact points 6 of the unit pattern 3A. The overlapping appears to have a significant effect on the aforementioned strength.

In some embodiments, the distance $W_3$ between adjacent unit patterns 3A and 3B can be in the range of about 1 to about 20 mm or any individual number within the range. In some embodiments, the distance $W_3$ can be in the range of about 2 to about 8 mm. The distance $W_3$ is the distance between a first shaded area 4 of the unit pattern 3A and the nearest first shaded area 4 of the unit pattern 3B. The distance $W_3$ is generally perpendicular to the first shaded area 4 of the unit pattern 3A and/or the first shaded area 4 of the unit patter 3B.

In some embodiments, the width of line $W_4$ of unit pattern 3 can be in the range of about 0.5 to about 1.5 mm. The width of line $W_4$ is generally perpendicular to the first centerline 31 and/or the second centerline 32 of the first shaded area 4 or the second shaded area 5, respectively. The width of the remainder of the first shaded areas 4 and second shaded areas 5 of the unit pattern being measured should be taken and averaged.

In some embodiments, the embossed area ratio (the value obtained by multiplying 100 by the area ratio of the embossed section 1 to the sum of the area of embossed section 1 and the area of nonembossed section 2 can be in the range of about 10 to about 50%. In some embodiments, the embossed area ratio can be in the range of about 20 to about 30%.

When each of the aforementioned conditions is satisfied, production of a nonwoven fabric with high adhesive strength and high mechanical strength as well as high bulkiness is made possible.

Figure 3:
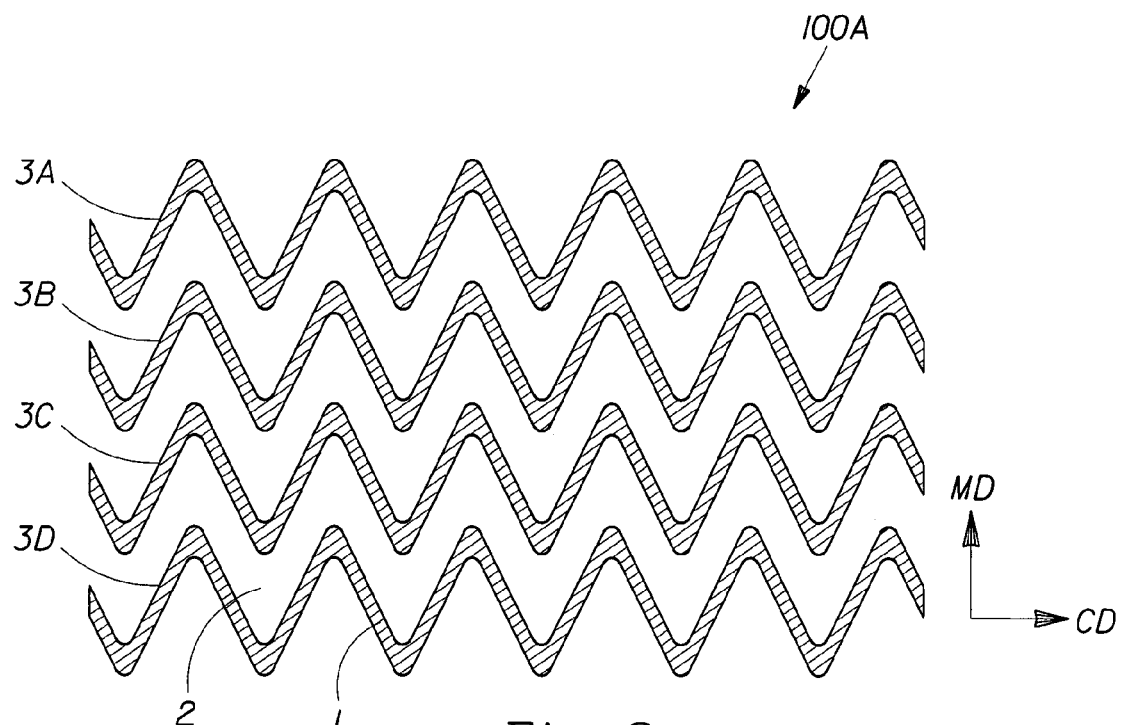
FIG. 3 is a partial top view of a modified example of the nonwoven fabric for use as the female component of the fastener of the application example shown in FIGS. 1B and 2.
Figure 4:
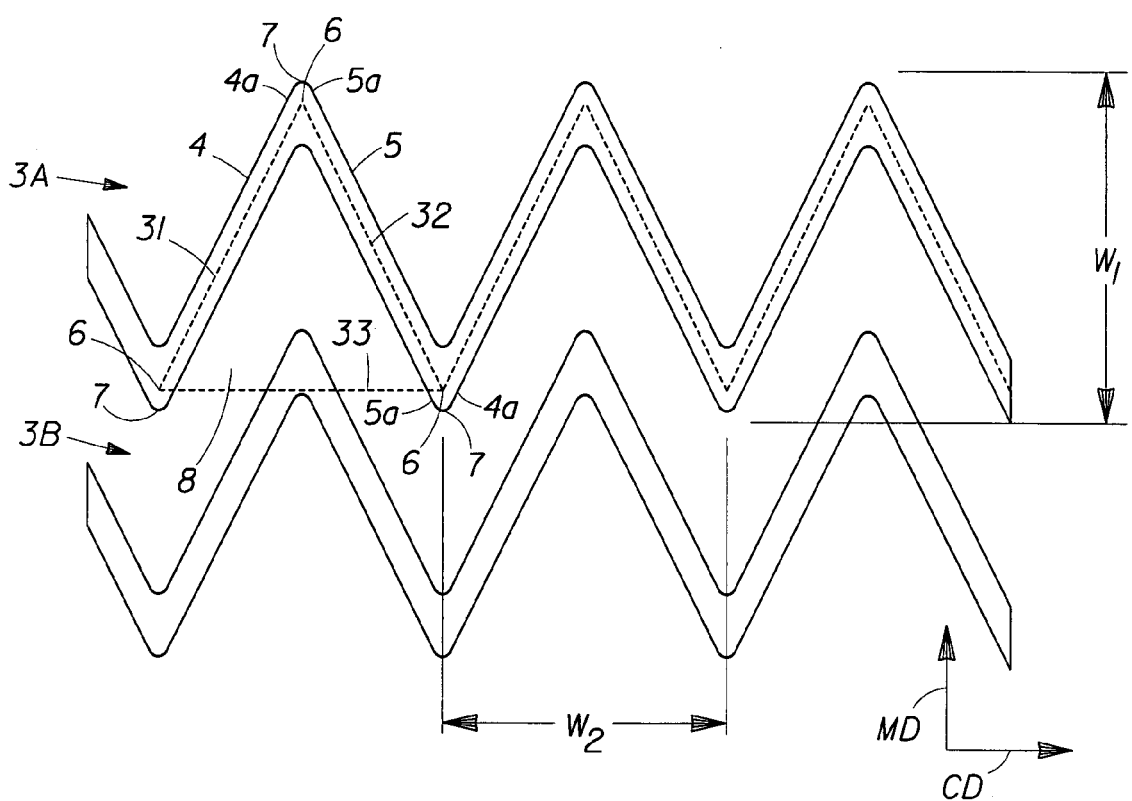
FIG. 4 is an enlarged partial view of the nonwoven fabric for use as the female component of the fastener of FIG. 3.

FIG. 3 shows another embodiment of a nonwoven fabric for use as the female component of the fastening system of the present invention. FIG. 4 is a partially enlarged view of the nonwoven fabric of FIG. 3. It should be noted that the components corresponding to FIGS. 1 and 2 are indicated by the same codes for FIGS. 3 and 4.

The nonwoven fabric 100A, in some embodiments, can have the same structure described previously. For example, as shown in FIG. 3, the nonwoven fabric 100A can be provided with embossed section 1 where a plurality of continuous zigzag unit patterns 3A, 3B, 3C, and 3D, are generally parallel to the CD direction of the embossing roll and are arranged in the MD direction at predetermined intervals. In contrast to the nonwoven fabric 100 discussed with regard to FIGS. 1B and 2, the nonwoven fabric 100A, in some embodiments, may comprise a unit pattern, e.g. 3A and 3B, comprising curves at apexes 7.

Figure 5:
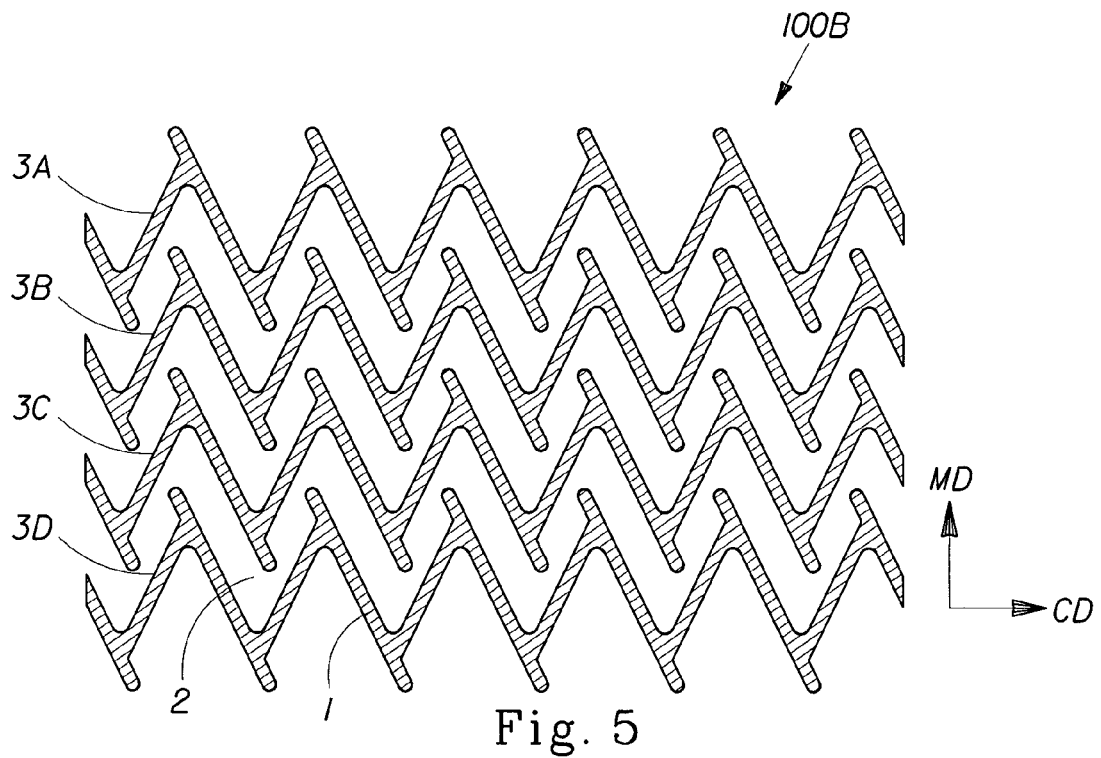
FIG. 5 is a partial top view of a different application example of the nonwoven fabric for use as the female component of the fastener of the present invention.
Figure 6:
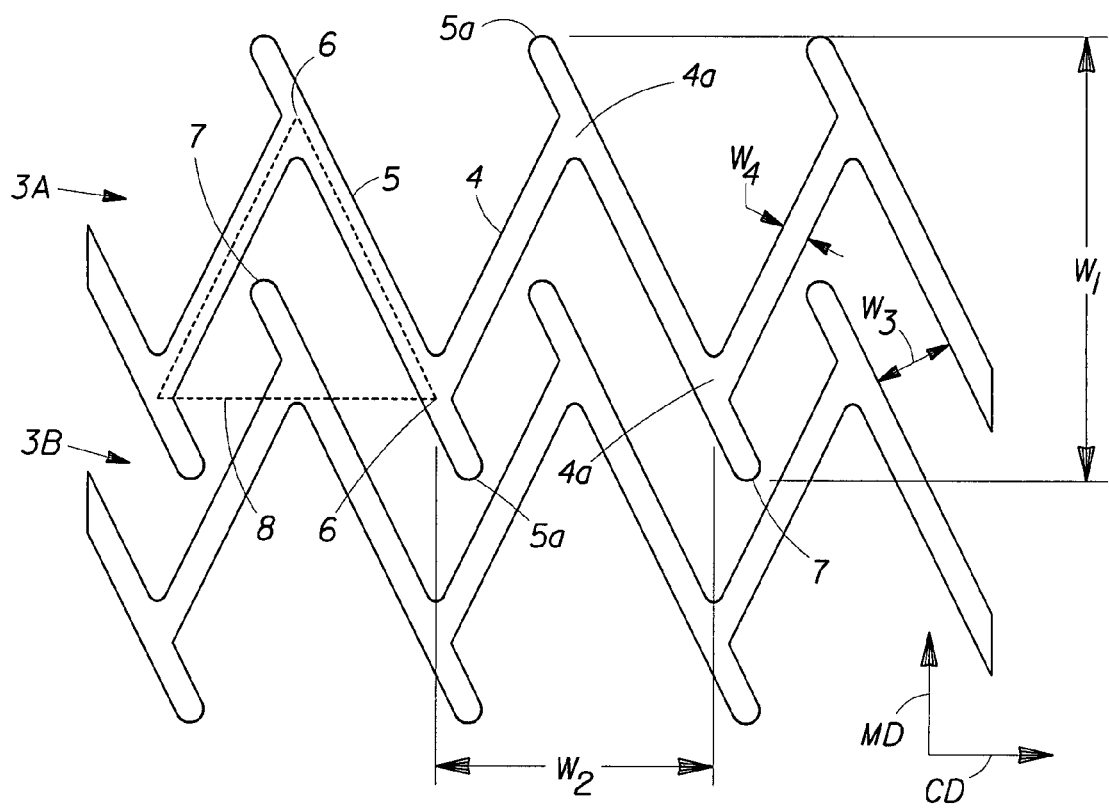
FIG. 6 is an enlarged partial view of the nonwoven fabric for use as the female component of the fastener of FIG. 5.

FIG. 5 is a partial top view of another embodiment of a nonwoven fabric for use as the female component of the fastening system of the present invention, and FIG. 6 is a partially enlarged view of the nonwoven fabric of FIG. 5. It should be noted that the components corresponding to FIGS. 1 and 2 are indicated by the same codes for FIGS. 5 and 6.

The nonwoven fabric 100B, in some embodiments, can have the same structure described previously. For example, as shown in FIG. 5, is the nonwoven fabric 100B can be provided with embossed section 1 comprising a plurality of continuous zigzag unit patterns 3A, 3B, 3C, and 3D, generally parallel to the CD direction of the embossing roll and arranged in the MD direction at predetermined intervals.

As shown in FIG. 6, unit patterns 3A and 3B may comprise a zigzag patterns where many first shaded areas 4 can be arranged at an angle with respect to the CD direction and slanted to one side at substantially the same angle with respect to the MD direction and many second shaded areas 5 can be arranged at an angle with respect to the CD direction and slanted toward the other side with respect to the MD direction and at substantially the same angle are arranged alternately.

As shown, in some embodiments, the second shaded area 5 can extend beyond the contact point 6. For example, as shown, the end member 5a can extend beyond the point of intersection between the first shaded area 4 and the second shaded area 5. For example, as shown, the apexes 7 correspond to the outermost points of the second shaded area of the unit pattern 3A. Because the end member 5a extends beyond the intersection between the first shaded area 4 and the second shaded area 5, the contact point 6 is disposed inward from the apex 7. In some embodiments, the apexes 7 can be the outermost points of the first shaded area 4.

As shown in FIG. 6, a part of unit pattern 3B can be contained inside the triangle 8 formed by three adjacent contact points 6 of the unit pattern 3A. For the embodiments shown in FIGS. 5 and 6, the ratio $W_1/W_2$ can be in the range of about 0.1 to about 10, or any individual number within the range, in some embodiments. In some embodiments, the ratio can be in the range of about 0.5 to about 2.0.

When the aforementioned conditions are satisfied, production of a female fastener component having a sufficient adhesive strength in all areas of peel strength, repeat peel strength, and tension shear strength as well as high mechanical strength in both of MD direction and CD direction can be made.

Figure 7:
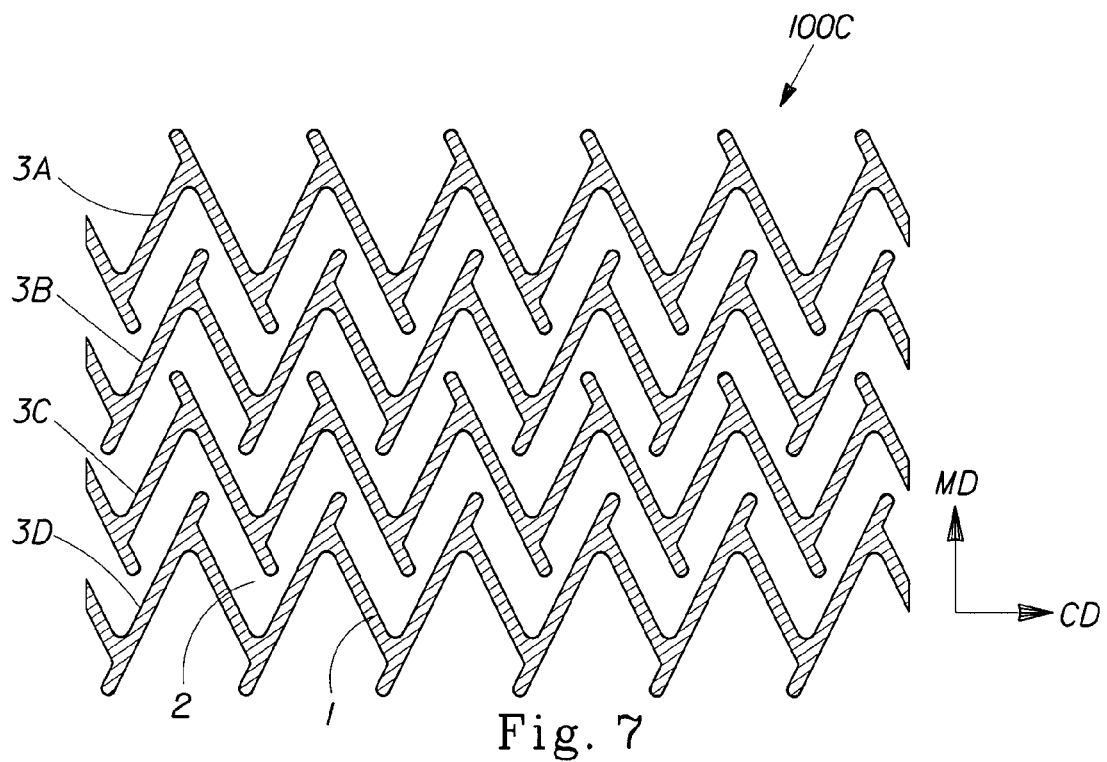
FIG. 7 is a partial top view of a modified example of the nonwoven fabric for use as the female component of the fastener of the application example of FIGS. 5 and 6.
Figure 8:
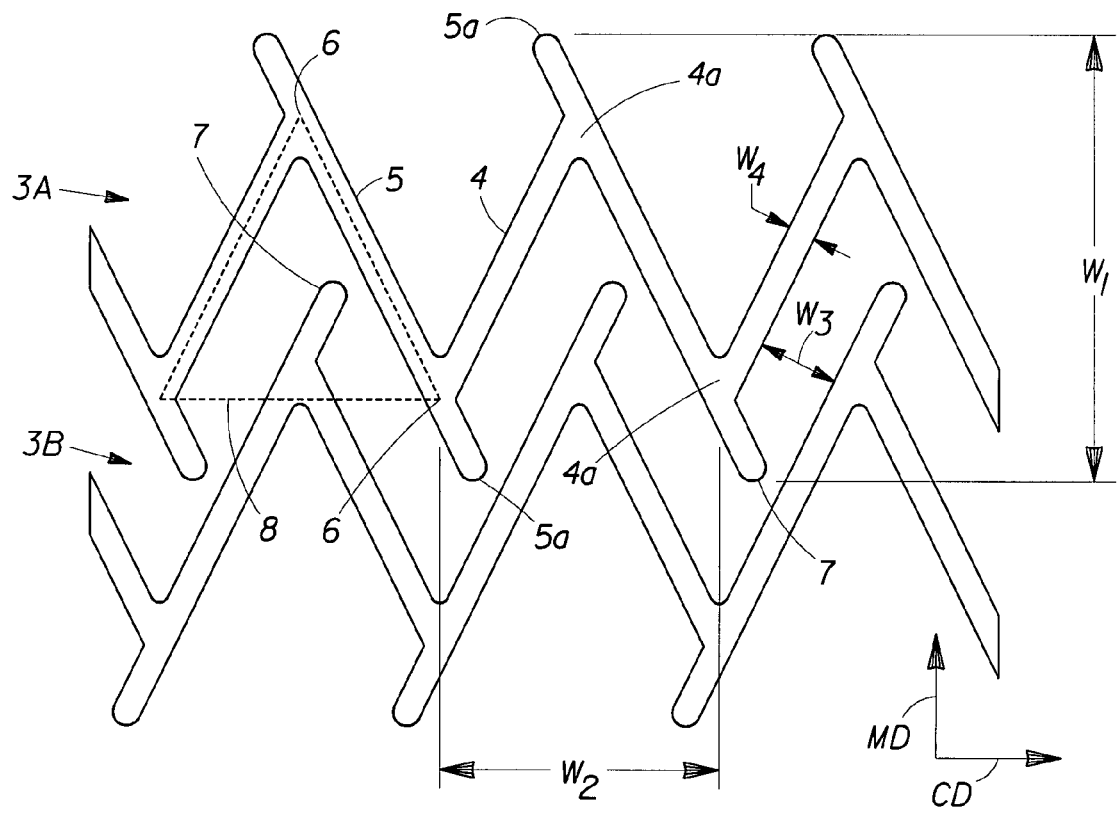
FIG. 8 is an enlarged partial view of the nonwoven fabric for use as the female component of the fastener of FIG. 7.

FIG. 7 is a partial top view of another embodiment for a nonwoven fabric 100C for use as the female component of a fastening system of the present invention, and FIG. 8 is an enlarged partial view of same. It should be noted that the components corresponding to FIGS. 5 and 6 are indicated by the same codes for FIGS. 7 and 8.

The nonwoven fabric 100C, in some embodiments, can have the same structure described previously. For example, and as shown in FIG. 7, the nonwoven fabric 100C can be provided with embossed sections 1 comprising unit patterns 3A, 3B, 3C, and 3D, generally parallel to the CD direction of the embossing roll are arranged in the MD direction at predetermined intervals. In some embodiments, the first shade areas 4 can extend beyond the contact points 6. In some embodiments, the second shaded areas 5 can extend beyond the contact points 6. In some embodiments, the unit pattern 3B may comprise first shade areas 4 which extend beyond the contact points 6, while the unit pattern 3A may comprise second shaded areas 5 which extend beyond the contact points 6. In yet other embodiments, a single unit pattern 3 may comprise at least one first shaded area 4 which extends beyond a contact point 6 and at least one second shaded area which extends beyond a contact point 6.

For example, as shown in FIG. 8, the nonwoven fabric 100C, may comprise, in some embodiments, the unit pattern 3A having a shape where the end member 5a of the second shaded area 5 extends beyond contact point 6, and the unit pattern 3B having a shape where the end member 4a of the first shaded area 4 extends beyond contact point 6. The unit patterns can be arranged alternately in the MD direction. As shown, in some embodiments, the first shaded area 4 and the second shaded area 5 can be mutually connected with end member 4a of the first shaded area 4 and the adjacent end member 5a of the second shaded area 5.

As shown, a part of unit pattern 3B can be contained inside the triangle 8 formed by adjacent three contact points 6 of the first shaded area 4 and the second shaded area 5 in unit pattern 3A. In some embodiments, the end member 5a of the second shaded area 5 of the unit pattern 3A can be contained inside a triangle formed by three adjacent contact points 6 of an adjacent unit pattern.

When structured as described above, production of a female fastener component having a sufficient fastening strength in all areas of peel strength, repeat peel strength, and tension shear strength as well as high mechanical strength in both the MD direction and CD direction can be made.

Figure 9:
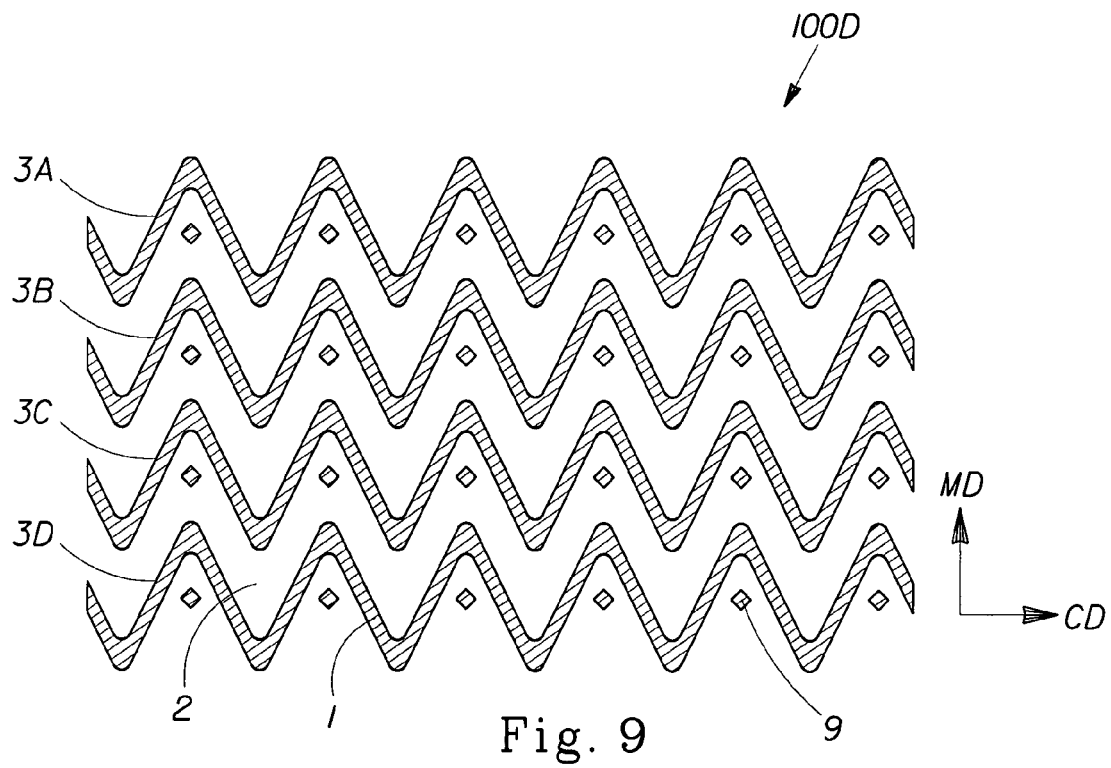
FIG. 9 is a partial top view of a different application example of the nonwoven fabric for use as the female component of the fastener of the present invention.
Figure 10:
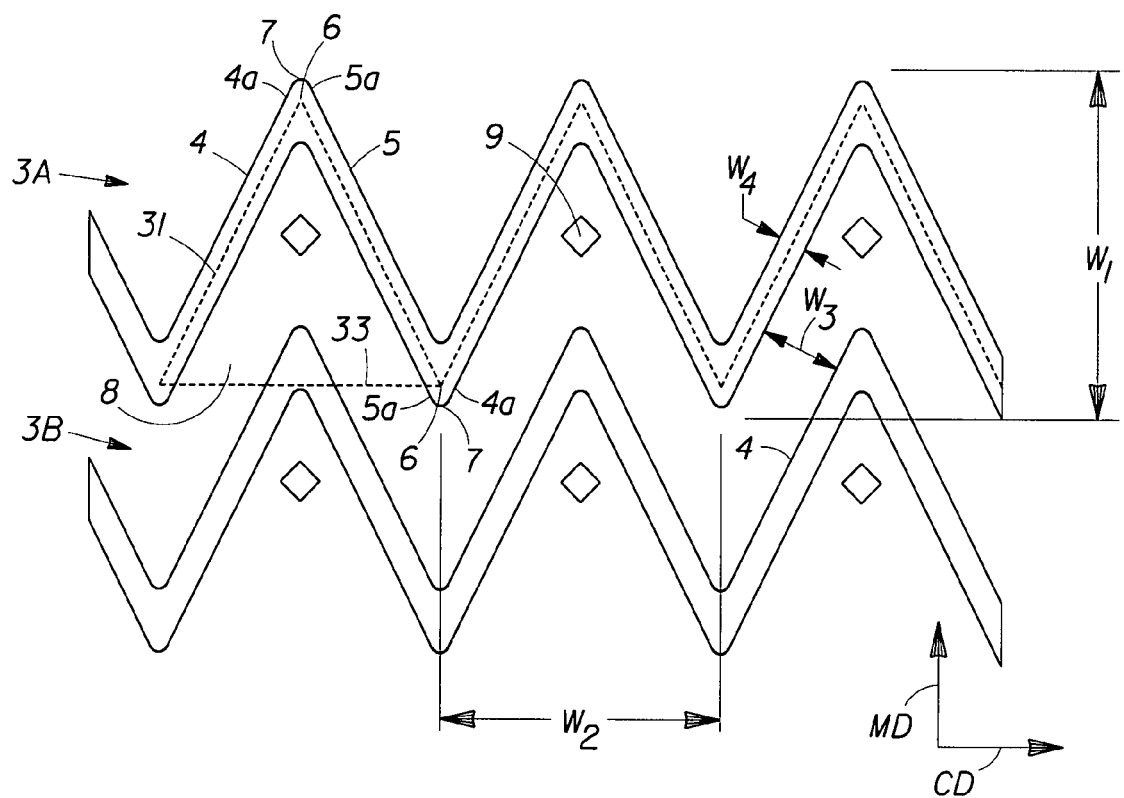
FIG. 10 is an enlarged partial view of the nonwoven fabric for use as the female component of the fastener of FIG. 9.

FIG. 9 is a partial top view of another embodiment of a nonwoven fabric 100D for use as the female component of the fastening system of the present invention, and FIG. 10 is a partially enlarged view of same. It should be noted that the components corresponding to FIGS. 1 and 2 are indicated by the same codes in FIGS. 9 and 10.

The nonwoven fabric 100D, in some embodiments, can have the same structure described previously. For example, the nonwoven fabric 100D can be provided with an embossed section 1 comprising unit patterns 3A, 3B, 3C, and 3D, generally parallel to the CD direction of the embossing roll which are arranged in the MD direction at predetermined intervals.

As shown in FIG. 10, in some embodiments, the unit patterns 3A and 3B may comprise a zigzag pattern where many first shaded areas 4 are arranged at an angle with respect to the CD direction and slanted to one side at substantially the same angle with respect to the MD direction. Additionally, as shown, in some embodiments, the unit patterns 3A and 3B may further comprise many second shaded areas 5 arranged at an angle with respect to the CD direction and slanted toward the other side with respect to the MD direction at substantially the same angle. As shown, in some embodiments the first shaded areas 4 and the second shaded areas 5 can be arranged alternately. The first shaded area 4 and the second shaded area 5 can be mutually connected with the end member 4a of the first shaded area 4 and the end member 5a of the second shaded area 5 as the contact point 6.

As shown in FIG. 10, a part of unit pattern 3B can be contained inside the triangle 8 formed by adjacent three contact points 6 of the first shaded area 4 and the second shaded area 5 (triangle 8 indicated by the dotted lines in FIG. 10) of the unit pattern 3A.

In some embodiments, a ratio of $W_1/W_2$ can be, in the range of about 0.1 to about 10, or any individual number within the range. In some embodiments, the ratio can be in the range of about 0.5 to about 2.0 as explained above.

Also, as shown, in some embodiments, a dot pattern 9 can be disposed between the unit patterns 3A and 3B. For example, as shown, in some embodiments, the dot pattern 9 can be disposed within the triangle 8. In some embodiments, the dot pattern 9 can be formed by thermal compression by an embossing roll. In these embodiments, the embossed section of the embossing roll may comprise unit pattern 3 and also dot pattern 9.

The position of dot pattern 9 can be any suitable position between the unit patterns 3A and 3B. The shape of dot pattern 9 can be any suitable shape. Examples of some suitable shapes include dots, ellipses, squares, rectangles, triangles, polygons, crescent, star, and the like. In some embodiments, the size of the dot is determined by taking factors such as fastening strength and bulkiness into consideration.

When structured as described above, production of the female fastener component having sufficient fastening strength in all areas of peel strength, repeat peel strength, and tension shear strength as well as high mechanical strength in both of MD direction and CD direction can be made.

The unit patterns discussed herein 3A, 3B, 3C, and 3D, can be configured in any suitable manner in accordance with the present invention. For example, the unit patterns 3C and 3D may be configured in any manner as discussed herein or any combination thereof. Similarly, the unit patterns 3A and 3B can be configured in any manner as discussed herein or any combination thereof.

The nonwoven fabric discussed heretofore may comprise a laminated structure, in some embodiments. For example, a nonwoven fabric may be used where the nonwoven fabric comprises crimped composite fibers, as discussed previously. The nonwoven fabric can be used as the uppermost layer and can be laminated to another layer on the backside.

Any suitable method can be utilized to create the laminate. For example, the laminate can be produced using a method where lamination is done in-line prior to bonding of the fibers of the nonwoven fabric. As another example, the laminate can be produced using a method where lamination is done off-line after the bonding of the fibers of the nonwoven.

For in-line lamination, in some embodiments, a first nonwoven fabric can be disposed superjacent to a second nonwoven fabric comprising crimped composite fibers. The first nonwoven and the second nonwoven can be thermally bonded to yield an integrated laminate structure. The first nonwoven may comprise a variety of polymers thermally fusible with the second nonwoven crimped composite fibers.

The first nonwoven fabric may comprise a spun-bonded nonwoven fabric, melt-blown nonwoven fabric, a carded nonwoven fabric, and combinations thereof.

Furthermore, a nonwoven fabric comprising the aforementioned crimped composite fiber having a different degree of crimping can be laminated as well.

The aforementioned polymers used for the nonwoven fabric material can be polyolefins, polyesters, polyamides, polyurethanes, etc. Suitable examples of polyolefins include propylene, polyethylene, and mixtures of the same. From the standpoint of spinnability, heat-resistance, and thermal fusion property, propylene can be preferred.

The first propylene type polymer and the second propylene type polymer for the crimped composite fibers mentioned previously can be used in this case as well. For example, when a melt-blown nonwoven fabric is used, use of propylenes with a melt-flow rate in the range of about 30 to about 3000 g/10 min, or any individual number within the range can be used. As another example, propylenes having a melt-flow rate in the range of about 400 to about 1500 g/10 min can be used. In some embodiments, the use of propylenes with the ratio of weight-average molecular weight to number-average molecular weight Mw/Mn can be in the range of about 2 to about 6.

Furthermore, for polyethylene, homopolymers of ethylene (either low-pressure method or high-pressure method may be used for production) and copolymers of ethylene and other α-olefins can be used for production. Suitable α-olefins include α-olefins with 3-20 carbon atoms such as propylene, 1-butene, 1-pentene, 1-hexene, 1-octene, 1-decene, 3-methyl-1-butene, 3-methyl-1-pentene, 3-ethyl-1-pentene, 4-methyl-1-pentene and 4-methyl-1-hexene. The α-olefins may be used independently for copolymerization or two or more different types may be used in combination for copolymerization.

In some embodiments, polyethylene can have a density in the range of about 880 to about 970 $kg/m^2$, or any individual number within the range. In some embodiments, the density can be in the range of about 910 to about 965 kg/m³. In the case of a melt-blown nonwoven fabric, in some embodiments, the melt-flow rate can be in the range of about 10 to about 400 g/10 min or any individual number within the range. In some embodiments, the melt-flow rate can be in the range of about 15 to about 250 g/10 min. The melt-flow rates are determined in part while the samples are under a temperature of 190° C. and load of 2160 g. Also, in some embodiments, the nonwoven fabric can have a ratio of the weight-average molecular weight to number-average molecular weight, Mw/Mn, in the range of about 1.5 to about 4.

Furthermore, for polyesters, aromatic polyesters having excellent strength, rigidity, etc., or biodecomposable aliphatic polyesters can be used for production. Suitable examples of aromatic polyesters include polyethylene terephthalate, polytrimethylene terephthalate, polytetramethylene terephthalate, etc. Suitable examples of aliphatic polyesters include polycondensates of a polyhydric carboxylic acid such as malonic acid, succinic acid, glutaric acid, adipic acid, sebacic acid, dodecanoic acid, malic acid, tartaric acid and citric acid and a polyhydric alcohol such as ethylene glycol, propylene glycol, butanediol, hexanediol, glycerol, and trimethylolpropane, ring-opening polymers such as lactide and caprolactone, and polycondensates of lactic acid, hydroxy acids such as hydroxybutyric acid and hydroxyvaleric acid, etc.

When the nonwoven fabric laminate is produced off-line, the type of the other layer laminated onto the second nonwoven comprising the composite fibers is not especially limited. For example, a layer comprising a knitted material, woven cloth, nonwoven fabric, film, etc., can be used. As for the lamination method, a thermal fusion process such as embossing finish, ultrasonic fusion, mechanical webbing methods such as needle punching and water jetting, adhesion with a hot-melt adhesive, etc., extrusion lamination when a film, etc., can be used.

The nonwoven fabric for use as the female component of the fastening system of the present invention has sufficient adhesive strength in all areas of peel strength, repeat peel strength, and tension shear strength as well as high mechanical strength in both the MD direction and CD direction. Also, the aforementioned nonwoven fabric has high bulkiness and softness as well as excellent spinnability and excellent antiflocking property.

A fastening system constructed in accordance with the present invention may be incorporated into a variety of consumer and commercial goods that may benefit from having a receiving component which comprises a bond pattern constructed in accordance with the present invention. In any of the embodiments described herein, the receiving component may be a separate element added to the commercial good. For example, the receiving member may be a discrete structure joined to any component (e.g., a topsheet, an absorbent core, a backsheet, a fastening system, a side panel, a cuff, etc.) of an absorbent article or other commercial good (e.g., a wrap, a medical product, etc.). Alternatively, the receiving component may be constructed as part or all of any element of the commercial good or fastener. For example, the receiving component may be constructed as part or all of any component (e.g., a topsheet, an absorbent core, a side panel, a backsheet, a fastening system, a cuff, etc.) of an absorbent article or other commercial good (e.g., a wrap, a medical product, etc.). Further, receiving component may be disposed in any suitable location on or in the commercial good or fastener. For example, the receiving component may be disposed on an outer-facing surface, wearer-facing surface of, or contained within the commercial good or fastener. As another example, an article having a wearer-facing surface and an outer-facing surface may comprise the fastening system of the present invention. The fastening system can be disposed on the wearer-facing surface or the outer-facing surface of the article. In some embodiments, the article can be selected from the group consisting of: an absorbent article, a diaper, a pant, an adult incontinence article, a feminine hygiene article, a body wrap, a bib, and a consumer good. For the sake of explanation, the receiving component of the present invention will be discussed in the context of disposable diapers.

Figure 16A:
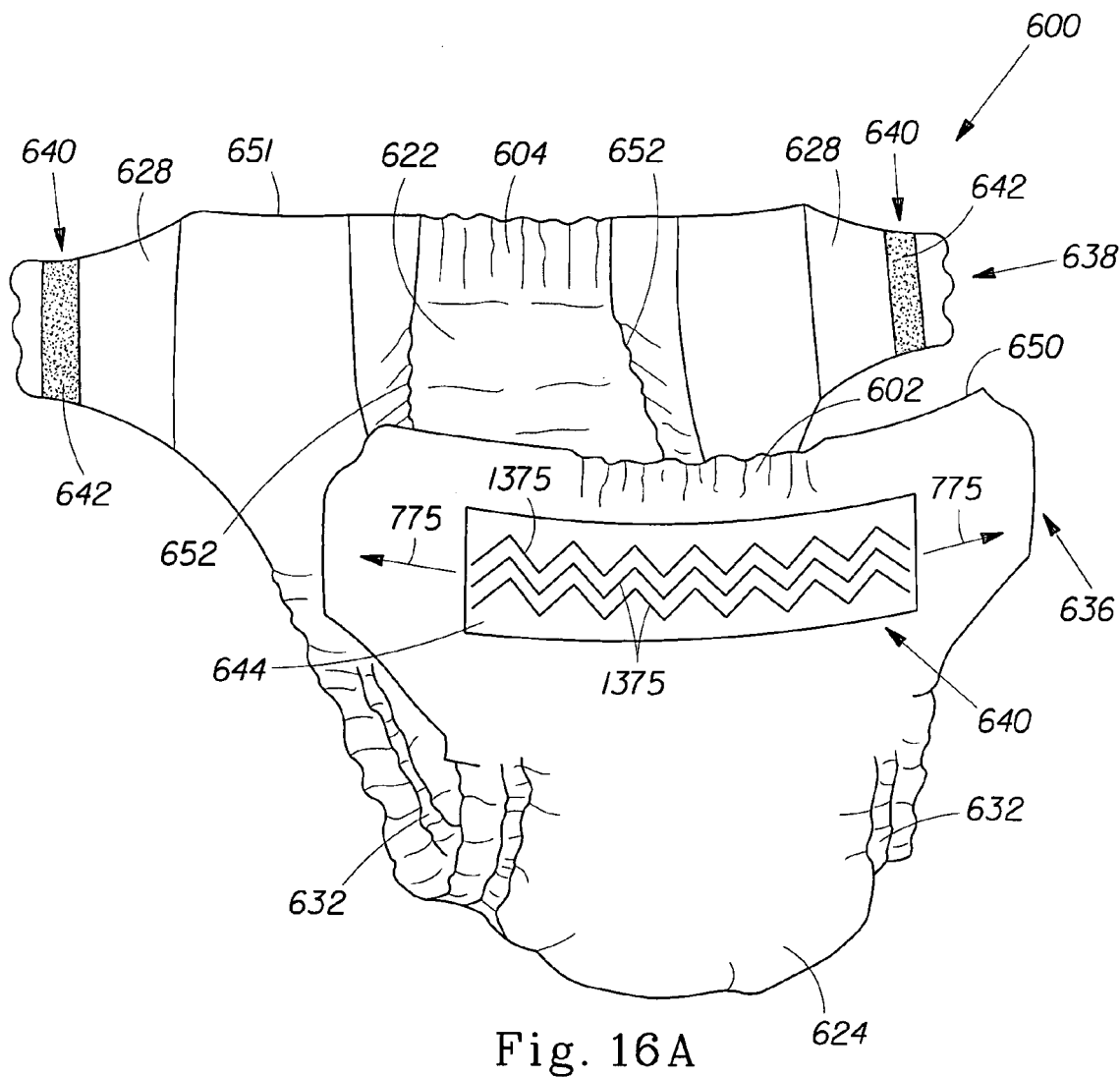
FIG. 16A is a perspective view showing a disposable absorbent article constructed in accordance with the present invention.
Figure 16B:
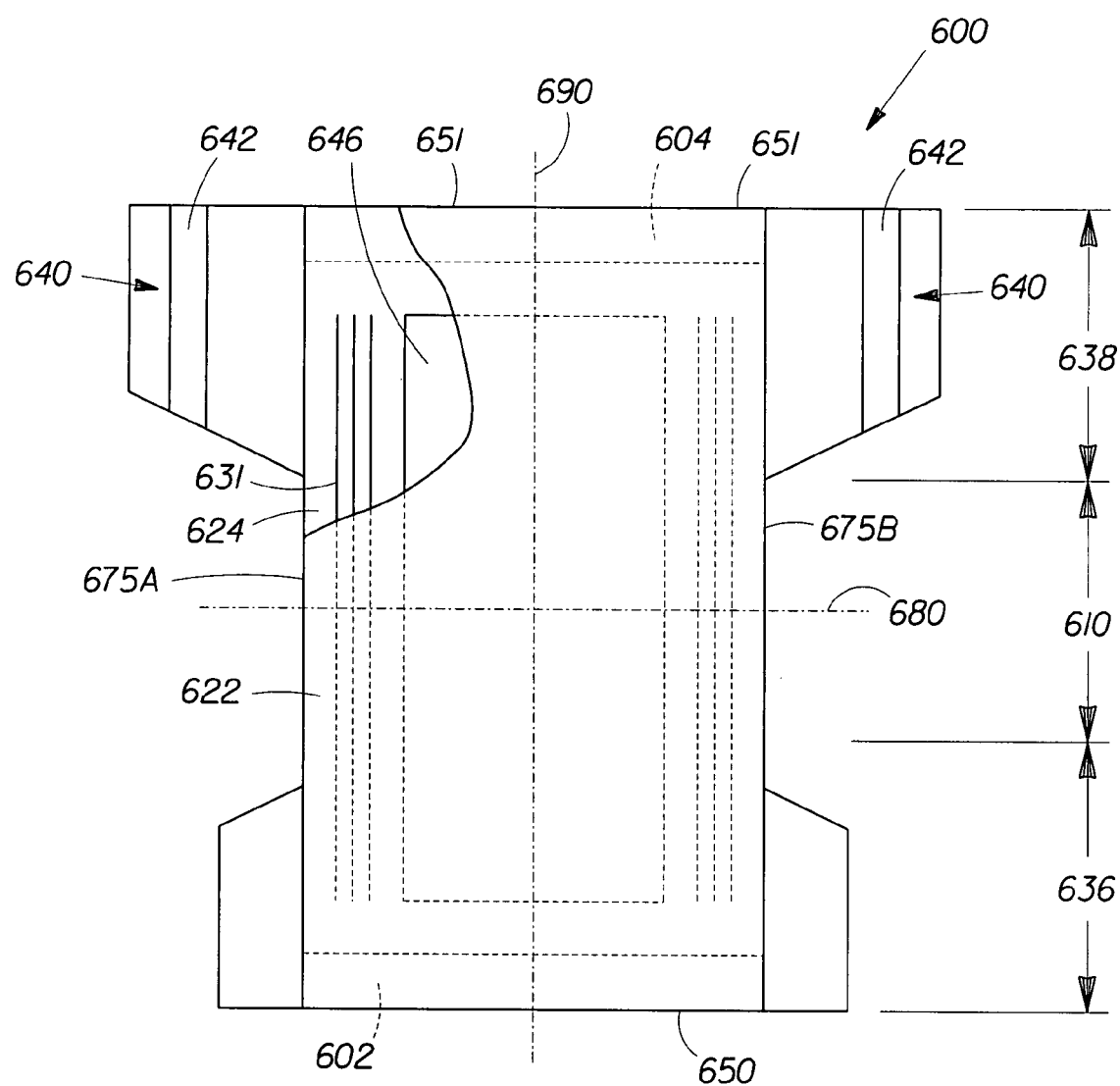
FIG. 16B is a plan view showing the disposable absorbent article of FIG. 16A in a flattened-out uncontracted state.

As shown in FIGS. 16A and 16B, a disposable absorbent article 600 may comprise a liquid pervious topsheet 622 and a backsheet 624 joined to at least a portion of the topsheet 622. The disposable absorbent article 600 further comprises an absorbent core 646 positioned between the topsheet 622 and the backsheet 624. The disposable absorbent article 600 may further comprise side panels 628, outer cuffs 632, inner cuffs 652, and waist features 630.

A portion of the periphery of the disposable absorbent article 600 can be defined by the longitudinal edges 675A and 675B; the first waist edge 650, and the second waist edge 651. The longitudinal edges 675A and 675B may run generally parallel to a longitudinal centerline 690 of the disposable absorbent article 600. The first waist edge 650 and the second waist edge 651 may run generally parallel to a lateral centerline 680 of the disposable absorbent article 600. The disposable absorbent article 600 may further comprise elastic leg features 631 which can be disposed adjacent to the longitudinal edges 675A and 675B.

The disposable absorbent article 600 may further comprise a first waist member 602 and a second waist member 604. The first waist member 602 and/or the second waist member 604 can be elastically extensible. As shown, in some embodiments, the first waist member 602 can be disposed adjacent the first waist edge 650. In some embodiments, the second waist member 604 can be disposed adjacent to the second waist edge 651. Generally, the first waist member 602 and/or the second waist member 604 can be under tension prior to joining to the disposable absorbent article 600. So, upon release of at least a portion of the tension applied to the first waist member 602 and/or the second waist member 604, a portion of the disposable absorbent article 600 joined thereto can corrugate. This corrugation of the disposable absorbent article 600 can allow the first waist member 602 and/or the second waist member 604 and the disposable absorbent article 600 to expand and contract about the waist of a wearer, thereby providing more comfort and improved fit to a wearer. Examples of suitable waist members 602 and/or 604 include those described in U.S. Pat. No. 4,515,595, U.S. Pat. No. 5,151,092, and U.S. Pat. No. 5,221,274. Although disposable diapers are generally constructed so as to have two elastic waist features, one positioned in a first waist region and one positioned in a second waist region, diapers can be constructed with a single elastic waist feature.

The disposable absorbent article 600 may further comprise outer cuffs 632 and inner cuffs 652 to improve containment of liquids and other body exudates. Each elasticized outer cuff 632 may include several different embodiments for reducing the leakage of body exudates in the leg regions. Outer cuffs 632 and inner cuffs 652 are further described in U.S. Pat. No. 3,860,003; U.S. Pat. No. 4,909,803; and U.S. Pat. No. 4,695,278.

As stated previously, the disposable absorbent article may further comprise a pair of side panels 628. As shown in FIG. 16B, the side panels 628 can extend outward from the first longitudinal edge 675A and the second longitudinal edge 675B of the disposable absorbent article 600. In some embodiments, the side panels 628 can be joined to the disposable absorbent article 600 in the second waist region 638, and in some embodiments, the side panels 628 can be joined to the disposable absorbent article 600 or in the first waist region 636. Alternatively, in some embodiments, the disposable absorbent article 600 may comprise a pair of side panels which are disposed in the second waist region 638 and a pair of side panels which are disposed in the first waist region 636. In some embodiments, the side panels 628 can form a portion of the leg openings when the disposable absorbent article 600 is fastened. The side panels 628 can form a portion of the leg openings which would be disposed on an outer surface of a leg of a wearer. A crotch region 610 of the disposable absorbent article 600 in conjunction with the first waist region 636 and the second waist region 638 can form a portion of the leg openings which would be disposed on an inner surface of the leg of the wearer. In some embodiments, the side panels 628 can be elastically extensible.

The disposable absorbent article 600 further comprises a fastening system 640 which joins at least a portion of a first waist region 636 with at least a portion of a second waist region 638, preferably to form leg and waist openings. The fastening system 640 also works with the waist members(s) 602 and/or 604 to maintain lateral tension in order to keep the disposable absorbent article 600 in place about the waist of the wearer. The fastening system 640 may comprise engaging components 642 which, in some embodiments, can be disposed on the side panels 628. The fastening system 640 may further comprise a receiving component 644 which, in some embodiments, is disposed in the first waist region 636.

Figure 16C:
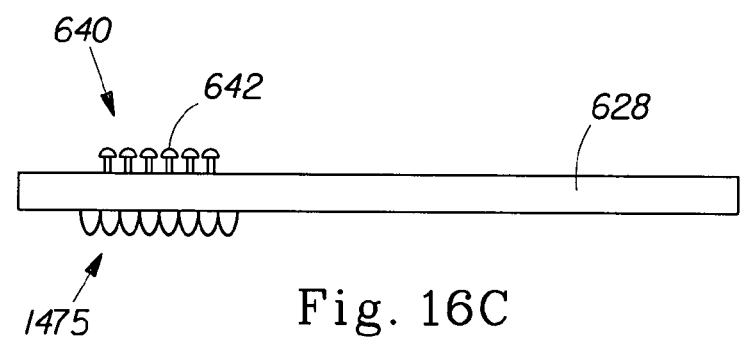
FIG. 16C is an elevation view showing another embodiment of a side panel of the disposable absorbent article of FIG. 16A.

As shown in FIG. 16C, in other embodiments, the fastening system 640 can include a plurality of fastening components on the side panels 628. For example, as shown, the side panel 628 may comprise the engaging component 642 which, in some embodiments, can include a plurality of engaging elements. Additionally, in some embodiments, the side panel 628 may further comprise a receiving component 1475 which is disposed opposite of the engaging component 642. One advantage of this arrangement is that the engaging component 642 can engage the receiving component 644 (shown in FIG. 16A) which is joined to the first waist region 636 or can join to the receiving component 1475 of the other side panel 628.

As shown in FIG. 16A, the receiving component 644 is disposed on the disposable absorbent article 600 such that the overlap of the bond lines 1375 is generally perpendicular to the primary direction of shear 775. As shown in FIG. 16A, the primary direction of shear 775 is an expected in use force which typically occurs once the disposable absorbent article 600 is in a fastened state. In some embodiments, the receiving component 644 can be disposed adjacent the first waist edge 650 in the first waist region 636 on an outer-facing surface of disposable absorbent article 600. In other embodiments, the receiving component 644 can be disposed adjacent the second waist edge 651 in the second waist region 638. In this embodiment, the engaging elements 642 can be disposed adjacent the first waist region 636. In some embodiments, receiving components 644 can be disposed on the side panels 628 and the engaging component can be disposed in the first waist region 636. In some embodiments, the receiving component 644 may comprise a plurality of discrete elements.

Any suitable engaging element 12 and/or 642 can be used in the present invention. An example of a suitable engaging element comprises hook fastening material. The hook fastening material can mechanically engage fibrous elements of the receiving element 644 so as to provide a secure closure. A hook fastening material according to the present invention may be manufactured from a wide range of materials. Suitable materials include nylon, polyester, polypropylene, or any combination of these materials, or other materials as are known in the art.

A suitable hook fastening material comprises a number of shaped engaging elements projecting from a backing such as the commercially available material designated Scotchmate™ brand No. FJ3402 available from Minnesota Mining and Manufacturing Company, St. Paul, Minn. Alternatively, the engaging elements may have any shape such as hooks, "T's", mushrooms, or any other shape as are well known in the art. An exemplary hook fastening material is described in U.S. Pat. No. 4,846,815. Another suitable hook fastening material comprises an array of prongs formed of thermoplastic material. Hot melt adhesive thermoplastics, in particular polyester and polyamide hot melt adhesives, are particularly well suited for forming the prongs of the hook fastening material. The prongs, in some embodiments, can be manufactured using a modified gravure printing process by printing the thermoplastic material in its molten state onto a substrate in discrete units, severing the material in a manner that allows stretching of a portion of the thermoplastic material prior to severance, and allowing the stretched molten material to "freeze" resulting in prongs. This hook fastening material and methods and apparatus for making such a hook fastening material are more fully detailed in European Patent Application 0 381 087.

The fastening system 640 may be the primary fastening system for joining the first and second waist regions 636 and 638. However, the fastening system 640 may be used alone or in conjunction with other fastening means such as tab and slot fasteners, tape fasteners, snaps, buttons, and the like to provide different fastening characteristics. For example, the fastening system 640 may provide the disposable absorbent article 600 with a disposal means for fastening the disposable absorbent article 600 in a configuration convenient for disposal. Further, secondary fastening means may provide the disposable absorbent article 600 with a means for adjusting fit or may increase the strength of the connection between the first waist region 636 and the second waist region 638.

The fastening system 640 can be prefastened in a package such that a caregiver or wearer may pull on the disposable absorbent article 600 when removed from the package. Alternatively, the fastening system 640 can be unfastened in the package such that the caregiver or wearer fastens the fastening system 640 while donning the disposable absorbent article 600. In yet another embodiment, a package may comprise both prefastened and unfastened disposable absorbent articles 600 for the convenience of the caregiver or the wearer.

Figure 17A:
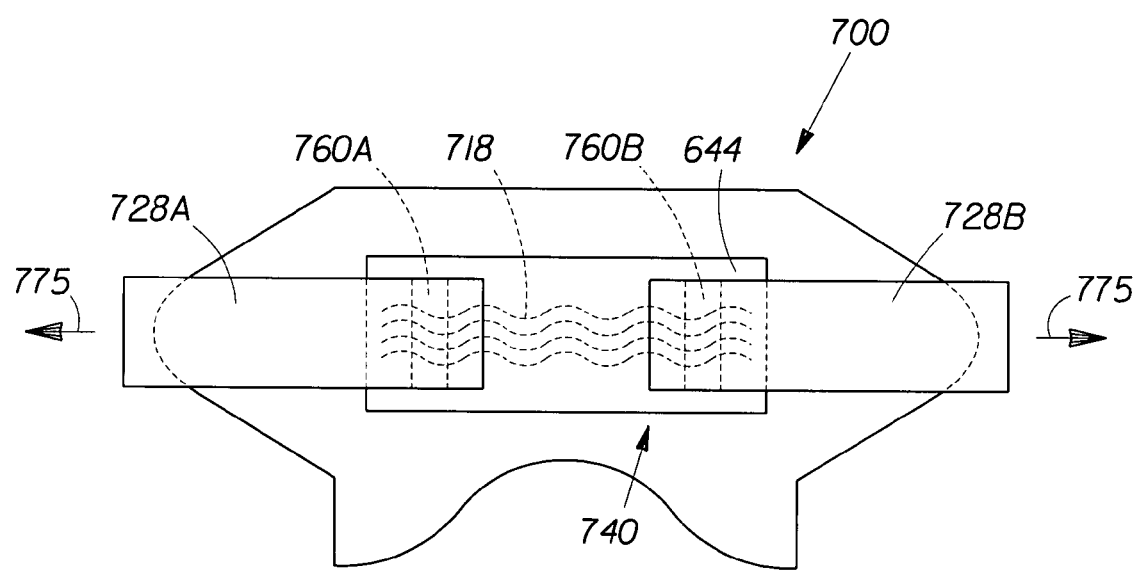
FIG. 17A is an elevation view showing a portion of the disposable absorbent article of FIG. 6 having its fastening system in a fastened state.

As shown in FIG. 17A, a disposable absorbent article 700 comprising a fastening system 740 is shown. The fastening system 740 comprises a first engaging component 760A disposed on a first side panel 728A and a second engaging component 760B disposed on a second side panel 728B. The first engaging component 760A and the second engaging component 760B can engage the receiving component 644 when fastened.

The receiving component 644 may comprise a plurality of bond lines 718 created in accordance with the present invention. Each of the plurality of bond lines 718 may comprise hills and valleys. As mentioned previously, the receiving component 644 can be disposed on the disposable absorbent article 700 such that the overlap between the bond lines is generally perpendicular to the primary direction of shear 775. So, receiving components of the present invention constructed similar to the receiving component (shown in FIGS. 1A-10) can be disposed on the disposable absorbent article 700 such that the CD direction of the receiving component is generally parallel to the primary direction of shear 775. Note that in FIGS. 1A-10 the receiving component was referred to as the female fastening component.

The primary direction of shear 775 is defined by the in use forces. Specifically, when the disposable absorbent article 700 is in a fastened state, the first side panel 728A and the second side panel 728B exert a force on the receiving component 644. The force can be caused, in part, by the elastomeric material of the side panels, if they are elastically extensible. Additionally, the shear forces may be caused by user or caregiver during application of the disposable absorbent article 700.

Figure 17B:
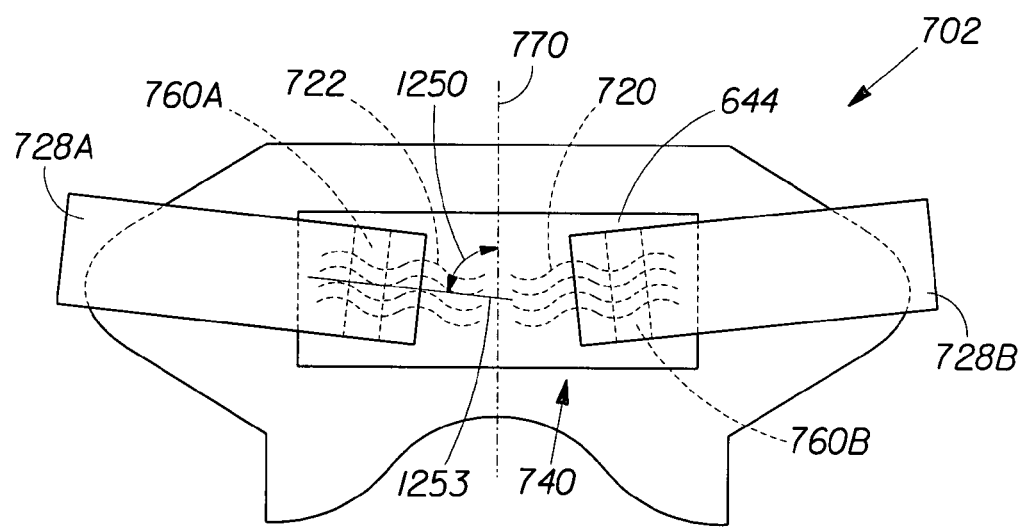
FIG. 17B is an elevation view showing a portion of the disposable absorbent article of FIG. 16A having its fastening system in a fastened state, wherein a receiving component of the fastening system is disposed on the disposable absorbent article to provide a visual alignment aid.

As shown in FIG. 17B, a disposable absorbent article 702 comprising a fastening system 740 is shown. Similar to the disposable absorbent article above, the first engaging component 760A and the second engaging component 760B can engage the receiving component 644 when fastened. The receiving component 644 may comprise a first plurality of bond lines 722 and a second plurality of bond lines 720. A portion of each of the first plurality of bond lines 722 overlaps a portion of each adjacent bond line. Similarly, a portion of each of the second plurality of bond lines 720 overlaps a portion of each adjacent bond line.

The first plurality of bond lines 722 may be angled such that they can provide a visual signal to a wearer of where to fasten the first engaging component 760A. Additionally, the second plurality of bond lines 720 may be angled such that they can provide a visual signal to a wearer of where to fasten the second engaging component 760B.

In some embodiments, the fastening angles 1250 can be in a range from between about 0 degrees to about 45 degrees or any individual number within that range. In other embodiments, the fastening angle 1250 can be between about 10 degrees and about 25degrees. In yet other embodiments, the fastening angle 1250 can be between about 15 degrees and about 20 degrees.

The fastening angle 1250 of the first plurality of bond lines 722 can be determined by performing straight line approximations for each of the bond lines within bond pattern of the first plurality of bond lines 722. A bond line can be considered to be a part of the first plurality of bond lines 722 if a portion of that bond line overlaps any portion of another bond line within the first plurality of bond lines 722. The straight line approximations for each of the bond lines within the first plurality of bond lines 722 can be averaged to determine a first orientation line 1253 for the first plurality of bond lines 722. The intersection between the first orientation line 1253 and a longitudinal axis 770 of the disposable absorbent article 702 defines the fastening angle 1250. The same analysis can be performed for the second plurality of bond lines 720.

Disposable absorbent articles may comprise many components, elements, members, etc. and can be constructed in a variety of manners. For example, the topsheet 622 (shown in FIG. 16B) and the backsheet 624 (shown in FIG. 16B) can have length and width dimensions generally larger than those of the absorbent core 626 (shown in FIG. 16B). The topsheet 622 (shown in FIG. 16B) and the backsheet 624 (shown in FIG. 16B) can extend beyond the edges of the absorbent core 626 (shown in FIG. 16B), thereby forming the periphery of the disposable absorbent article 600 (shown in FIG. 16B). The topsheet 622 (shown in FIG. 16B), the backsheet 624 (shown in FIG. 16B), and the absorbent core 626 (shown in FIG. 16B) may include many different materials and may be assembled in a variety of well known configurations, exemplary diaper materials and configurations are described generally in U.S. Pat. No. 3,860,003, U.S. Pat. No. 5,151,092, and U.S. Pat. No. 5,221,274.

Any topsheet compatible with the present invention which is known in the art can be used in the present invention. A suitable material for a topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. As an example, a material suitable for use in a topsheet comprises a web of staple-length polypropylene fibers is manufactured by Veratec, Inc., a Division of International Paper Company, of Walpole, Mass. under the designation P-8.

Some examples of suitable topsheets are described further in U.S. Pat. No. 3,929,135; U.S. Pat. No. 4,324,246; U.S. Pat. No. 4,342,314; U.S. Pat. No. 4,463,045; U.S. Pat. No. 5,006,394; U.S. Pat. No. 4,609,518; U.S. Pat. No. 4,629,643. Any portion of the topsheet may be coated with a lotion as is known in the art. Examples of suitable lotions include those described in U.S. Pat. No. 5,607,760; U.S. Pat. No. 5,609,587; U.S. Pat. No. 5,635,191; U.S. Pat. No. 5,643,588; U.S. Pat. No. 5,968,025; U.S. Pat. No. 6,716,441; and PCT Publication No. WO 95/24173.

Further, the topsheet may be fully or partially elastically extensible or may be foreshortened so as to provide a void space between the topsheet and the absorbent core. Exemplary structures including elasticized or foreshortened topsheets are described in more detail in U.S. Pat. No. 4,892,536; U.S. Pat. No. 4,990,147; U.S. Pat. No. 5,037,416; and U.S. Pat. No. 5,269,775.

A suitable backsheet for use in the disposable absorbent article of the present invention may comprise a laminated structure. For example, the backsheet may comprise a first backsheet layer and a second backsheet layer. The second backsheet layer can be impervious to liquids (e.g., urine) and comprise a thin plastic film such as a thermoplastic film having a thickness, for example, of about 0.012 mm (0.5 mils) to about 0.051 mm (2.0 mils). Suitable backsheet films include those manufactured by Tredegar Corporation, based in Richmond, Va., and sold under the trade name CPC2 film. Either the first backsheet layer and/or the second backsheet layer may include breathable materials which permit vapors to escape from the pull-on garment while still preventing exudates from passing through the backsheet. Suitable breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746; U.S. Pat. No. 5,938,648; U.S. Pat. No. 5,865,823; and U.S. Pat. No. 5,571,096.

The backsheet, or any portion thereof, may be elastically extensible in one or more directions. In one embodiment, the backsheet may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801. In alternate embodiments, the backsheet may comprise elastic films, foams, strands, or combinations of these or other suitable materials with nonwovens or synthetic films.

A suitable absorbent core for use in the present invention may comprise any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Suitable exemplary absorbent structures for use as the absorbent core are described in U.S. Pat. No. 4,610,678; U.S. Pat. No. 4,673,402; U.S. Pat. No. 4,834,735; U.S. Pat. No. 4,888,231; U.S. Pat. No. 5,137,537; U.S. Pat. No. 5,147,345; U.S. Pat. No. 5,342,338; U.S. Pat. No. 5,260,345; U.S. Pat. No. 5,387,207; and U.S. Pat. No. 5,625,222.

The backsheet may be joined to the topsheet, the absorbent core, or any other element of the disposable absorbent article by any attachment means known in the art. For example, the attachment means may include a uniform continuous layer of adhesive, a patterned layer of adhesive, or an array of separate lines, spirals, or spots of adhesive. Some suitable attachment means are disclosed in U.S. Pat. No. 4,573,986; U.S. Pat. No. 3,911,173; U.S. Pat. No. 4,785,996; and U.S. Pat. No. 4,842,666. Examples of suitable adhesives are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

Various sublayers may be disposed between the topsheet and the backsheet. The sublayer may be any material or structure capable of accepting, storing or immobilizing bodily exudates. Thus, the sublayer may include a single material or a number of materials operatively associated with each other. Further, the sublayer may be integral with another element of the pull-on disposable absorbent article or may be one or more separate elements joined directly or indirectly with one or more elements of the disposable absorbent article. Further, the sublayer may include a structure that is separate from the absorbent core or may include or be part of at least a portion of the absorbent core.

Suitable exemplary materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and, more specifically, having pores greater than about 1.0 mm in diameter.) One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. No. 6,680,422 and U.S. Pat. No. 5,941,864. Further, the sublayer, or any portion thereof, may include or be coated with a lotion or other known substances to add, enhance or change the performance or other characteristics of the element.

Embodiments of the present invention may also include pockets for receiving and containing waste, spacers which provide voids for waste, barriers for limiting the movement of waste in the article, compartments or voids which accept and contain waste materials deposited in the pull-on disposable absorbent article, and the like, or any combinations thereof. Examples of pockets and spacers for use in absorbent products are described in U.S. Pat. No. 5,514,121; U.S. Pat. No. 5,171,236; U.S. Pat. No. 5,397,318; U.S. Pat. No. 5,540,671; U.S. Pat. No. 6,168,584; U.S. Pat. No. 5,306,266; and U.S. Pat. No. 5,997,520. Examples of compartments or voids in an absorbent article are disclosed in U.S. Pat. No. 4,968,312; U.S. Pat. No. 4,990,147; U.S. Pat. No. 5,062,840; and U.S. Pat. No. 5,269,755. Examples of suitable transverse barriers are described in U.S. Pat. No. 5,554,142; PCT Patent WO 94/14395; and U.S. Pat. No. 5,653,703. Examples of other structures suitable for management of low viscosity feces are disclosed in U.S. Pat. No. 5,941,864; U.S. Pat. No. 5,977,430; and U.S. Pat. No. 6,013,063.

Embodiments of the present invention may include acquisition/distribution layers which can be configured to distribute moisture from a wetness event to moisture responsive members within the disposable absorbent article. Examples of suitable acquisition/distribution layers are described in U.S. Pat. No. 5,460,622, U.S. Patent Application Publication No. 2005/0027267, and U.S. Patent Application Publication No. 2005/009173.

Embodiments of the present invention may include a dusting layer which is well known in the art. Examples of suitable dusting layers are discussed in U.S. Pat. No. 4,888,231.

EXAMPLES

The present invention is further explained specifically with examples below, but the present invention is not limited by the examples shown below. It should be noted that adhesive strength (tension shear strength and peel strength), mechanical strength (tensile strength in MD and CD), basis weight, etc., were measured according to the methods described below in examples shown below.

Tensile Testing

Shear Force, Peel Force, and Breaking Force are all measured on a constant rate of extension tensile tester with computer interface (a suitable instrument is the MTS Alliance using Testworks 4.0 Software, as available from MTS Systems Corp., Eden Prairie, Minn.) using a load cell for which the forces measured are within 10% to 90% of the limit of the cell. Both the movable (upper) and stationary (lower) pneumatic jaws are fitted with rubber faced grips, wider than the width of the test specimen.

Testing is conducted in a lab maintained at $23\pm2°$ C. and $50\pm2\%$ relative humidity. Materials should be equilibrated in this environment for at least two hours before testing begins. All results are reported in Newtons (N) as the average of 10 replicates.

A standard mushroom-shaped mechanical fastener (hook) tape is used for the shear and peel testing. The hook material is made of polypropylene with hooks having a mean height of 0.4 mm, a mean end size of 0.2 mm by 0.3 mm, and an approximate density of 220 hooks/$cm^2$.

Shear Force

The shear force is measured using the equipment described above under tensile testing.

Identify the cross direction (CD) and machine direction (MD) of the female fastener (loop) material. Cut a test specimen that has a dimension of 50 mm in the MD (width) by 70 mm in the CD (length). Mount the loop specimen onto a steel plate (dimensions: 100 mm length by 50 mm width by 1 mm thick) using two-sided tape such that the fastening side of the specimen faces away from the plate, the specimen's CD is parallel to the length of the plate, and specimen's edges are flush with the left, right and bottom edges of the plate.

Identify the CD and MD of the standard hook material. Cut a specimen with the dimensions of 25 mm in the MD and 13 mm in the CD. Mount the hook specimen on a strip of copy paper (75 gsm; dimensions: 25 mm width by 100 mm length) using two-sided tape, such that the hook side of the specimen faces away from the paper strip, the specimen's CD is parallel to the length of the paper strip, and the specimen's edges are flush with the left, right and top edges of the paper strip.

Place the metal plate on a flat bench with the loop specimen facing upward with the top (i.e. the end of the plate not covered by the loop specimen) oriented away from the operator. Place the hook specimen, hooks down, onto the center of the loop specimen with the CD of the hook specimen parallel to the CD of the loop specimen, and the lead of the paper strip pointing toward the operator. The assembly is then rolled with a 5 kg roller for 5 cycles (1 cycle being defined as a forward stroke and a return stroke).

Set the gage length of the tensile tester to 75 mm and zero the cross head. Place the top of the metal plate into the upper grip faces such that it is centered horizontally in the grip faces with the lead of the paper strip hanging downward. Align the specimen assembly vertically and close the upper grip faces. Insert the lead of the paper strip into the lower grip faces and close. Zero the load cell.

Start the tensile tester and data collection. The jaws are moved apart at a rate of 300 mm/min until the hook and loop assembly is completely disengaged. The maximum shear force (N) is then calculated by the software from the resulting force/extension curve.

Peel Force and Repeat Peel Force

The peel force is measured using the equipment described above under tensile testing.

Identify the cross direction (CD) and machine direction (MD) of the female fastener (loop) material. Cut a test specimen that has a dimension of 50 mm in the MD (width) by 100 mm in the CD (length).

Identify the CD and MD of the standard hook material. Cut a specimen with the dimensions of 25 mm in the MD and 13 mm in the CD. Mount the hook specimen on a strip of copy paper (75 gsm; dimensions: 25 mm width by 100 mm length) using two-sided tape, such that the hook side of the specimen faces away from the paper strip, the specimen's CD is parallel to the length of the paper strip, and the specimen's edges are flush with the left, right and bottom edges of the paper strip.

Place the loop specimen on a flat bench with the loops facing upward. Place the hook specimen, hooks down, onto the center of the loop specimen with the CD of the hook specimen parallel to the CD of the loop specimen, and the lead of the paper strip pointing away from the operator. The assembly is then rolled with a 5 kg roller for 5 cycles (1 cycle being defined as a forward stroke and a return stroke). Carefully bend the lead of the paper strip 180° back toward the operator, with the crease directly adjacent to the hook specimen. Mark the loop specimen directly above the hook specimen so that the hook specimen can be readily reattached at the same location for the repeat peel test.

Set the gage length of the tensile tester to 75 mm and zero the cross head. Place the top of the loop material into the upper grip faces such that it is centered horizontally in the grip faces with the lead of the paper strip hanging downward. Align the specimen assembly vertically and close the upper grip faces. Insert the lead of the paper strip into the lower grip faces and close. Zero the load cell.

Start the tensile tester and data collection. The jaws are moved apart at a rate of 300 mm/min until the hook and loop assembly is completely disengaged. The maximum peel force (N) is then calculated by the software from the resulting force/extension curve.

For the repeat peel, the two pieces are removed from the tensile tester, the hook specimen is reengaged at the same location on the loop specimen, rolled for 5 cycles, and again peeled as described above. In like fashion, a third peel is also performed. The maximum peel force for each of the three peels are recorded separately.

Mechanical Strength

The breaking force is measured using the equipment described above under tensile testing.

Identify the cross direction (CD) and machine direction (MD) of the female fastener (loop) material. Cut a test specimen that has a dimension of 25 mm in the MD by 200 mm in the CD.

Set the gage length on the tensile tester to 100 mm. Zero the cross head and load cell. Insert the specimen into the upper grip faces, aligning it vertically within the upper and lower jaws, and close the upper grip faces. Insert the specimen into the lower grip faces and close. The specimen should be under enough tension to eliminate any slack, but less than 0.05 N of force measured at the load cell.

The jaws are moved apart at a rate of 100 mm/min until the specimen ruptures. The maximum breaking force (N) is calculated by the software from the resulting force/extension curve.

Repeat the above procedure with a specimen cut to the dimension of 25 mm in the CD by 200 mm in the MD. Record CD and MD breaking forces separately.

(3) Basis weight

Basis weight of the nonwoven is measured gravimetrically. Ten pieces of material are stacked and then cut to 100 mm by 100 mm using a steel blade die and hydraulic press. The stack is then weighed and the basis weight calculated as $g/m^2$.

(4) Number of Crimps

Number of crimps was measured according to the procedure explained below. It should be noted that with the exception of the procedure shown below, measurements were done according to the specification of JIS L1015.

First, lines with a spatial separation of 25 mm were formed on a piece of glossy paper with a smooth surface. The two ends of each fiber were carefully removed from the nonwoven fabric prior to thermal compression treatment by an embossing roll such that crimping was not lost and were applied onto the aforementioned paper with a relaxation of 25±5% for the spatial separation.

The aforementioned each test piece was applied to the chuck of the crimping tester, the paper was removed, and the distance between chucks (spatial distance) (mm) during the initial load (0.18 mN×displayed tex number) was read.

The number of crimps at the time was counted and the number of crimps per distance of 25 mm was obtained and the mean value of 20 times was used. The number of crimps was obtained as the total peaks and valleys were counted and divided by 2.

(5) Thickness (Caliper)

Thickness of the nonwoven is measured using a constant-pressure thickness meter (Ozaki Manufacturing Co., Japan) fitted with a 16 mm diameter caliper head, which exerts a confining force of 3.6 $g/cm^2$. Readings are recorded at 30 sec.±5 sec after the force is applied. A sample is cut into five 100 mm by 100 mm test specimens. The caliper is measured at three different locations on each specimen and the result is reported in mm as the average of the 15 measurements.

Application Example 1

Composite hot-melt spinning was carried out on a polypropylene homopolymer having a melting point of 162° C. and MFR=60 g/10 min (According to the specification of ASTM D1238, measurement was made at a temperature of 230° C. and under load of 2.16 kg. The same applies below unless otherwise specified.) and a propylene-ethylene random copolymer having a melting point of 142° C. and MFR=60 g/10 min by means of the spun-bonding method so as to produce a web comprising a side-by-side composite fiber (fiber size of 2.5 denier) with a weight ratio of 20/80. At this time, an adjustment was made for the molding conditions so that a final basis weight of the nonwoven fabric of 45 g/m² could be achieved. In this case, the number of crimps in the fiber was 25 crimps/25 mm.

(Adjustment and Evaluation of the Nonwoven Fabric for Use as the Female Component of a Fastener)

The aforementioned web produced was passed between an embossing roll, the surface of which was engraved with the pattern shown in FIG. 1, and a flat roll, compression was provided under heat to produce a nonwoven fabric for use as the female component of a fastener with a basis weight of 45 g/m². In this case, the temperature of the embossing roll and the temperature of the flat roll were both 125° C. and the line pressure was 30 N/mm.

The pattern shown in FIG. 1B has dimensions of: $W_1$=11.5 mm, $W_2$=9.3 mm ($W_1/W_2$=1.2), $W_3$=3.2 mm, $W_4$=1.0 mm, and the embossed area ratio is 24%. Furthermore, a part of the unit pattern extending in the MD direction is contained inside the triangle formed by the adjacent three contact points of the first shaded area and the second shaded area in the aforementioned unit pattern.

The adhesive strength, mechanical strength and thickness of the aforementioned nonwoven fabric for use as the female component of the fastener were measured and evaluated. The results obtained are shown in Table 1 below.

Comparative Example 1

A propylene-ethylene random copolymer having a melting point of 142° C. and MFR=60 g/10 min alone was used and hot-melt spinning was performed by a spun-bonding method and a nonwoven fabric for use as the female component of the fastener was produced as in the case of the aforementioned Application Example 1. With regard to the nonwoven fabric for use as the female component of the fastener produced above, the adhesive strength, mechanical strength and thickness were measured and evaluated. The results obtained are shown in Table 1 below.

Comparative Example 2

Figure 11:
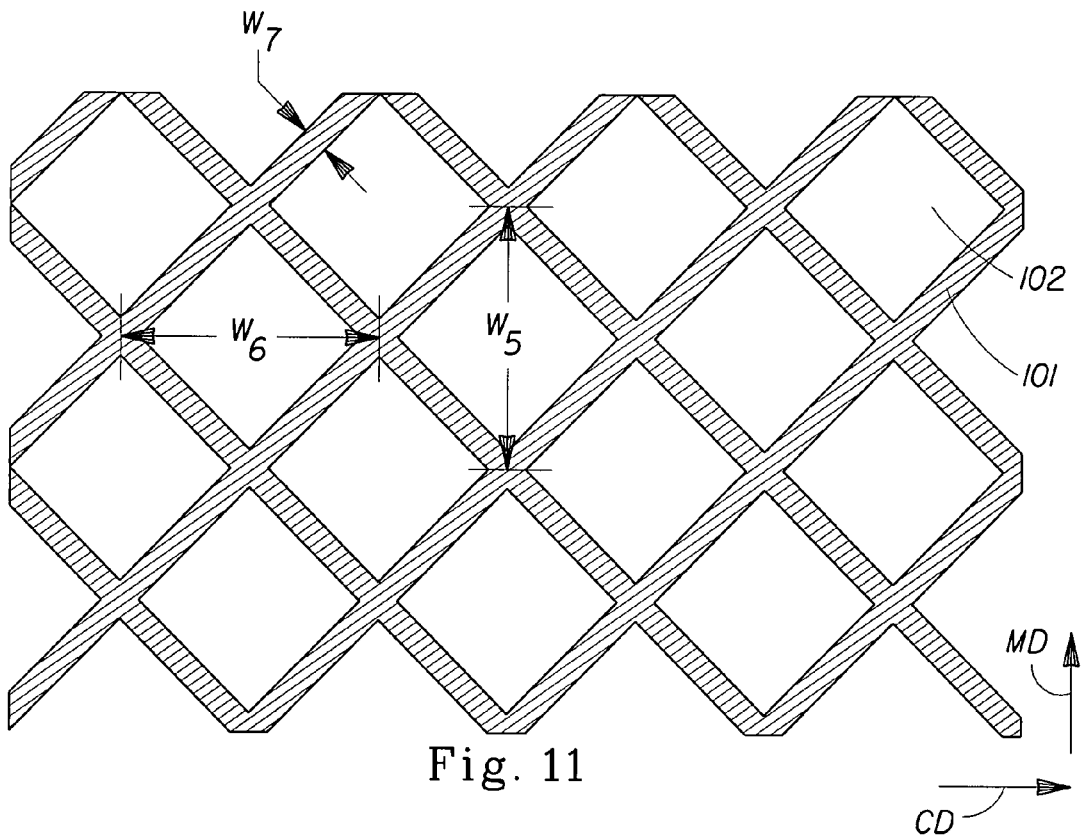
FIG. 11 is a partial top view of the nonwoven fabric for use as the female component of the fastener of Comparative Example 2.

An embossing roll engraved with the pattern shown in FIG. 11 on the surface was used and a nonwoven fabric for use as the female component of the fastener was produced as in the case of Application Example 1. As shown in FIG. 11, the embossed pattern is a diamond pattern arranged in the MD direction and CD direction. The embossed section 101 had a distance between nodes in MD direction, $W_5$=11.1 mm, distance between nodes in CD direction, $W_6$=11.1 mm, line width $W_7$=1 mm and embossed area ratio of 24%.

The fastening strength, mechanical strength, and thickness of the aforementioned nonwoven fabric for use as the female component for fastener produced above were measured and evaluated. The results obtained are shown in Table 1 below.

Comparative Example 3

Figure 12:
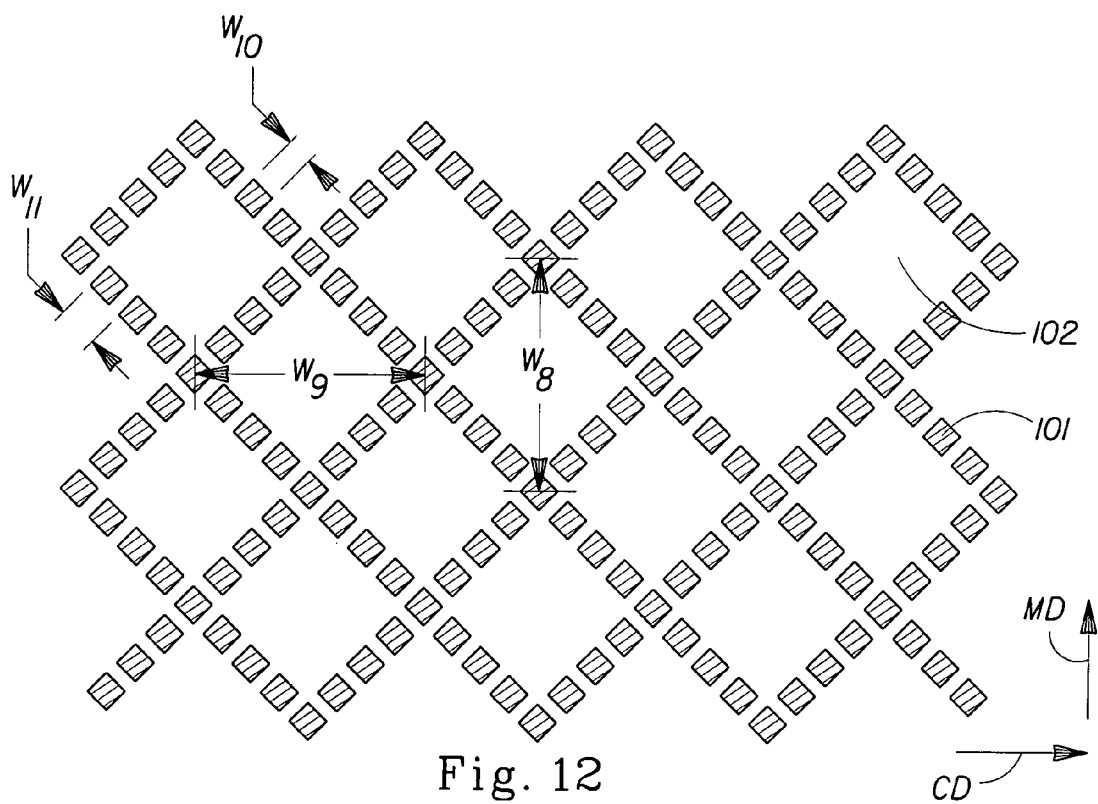
FIG. 12 is a partial top view of the nonwoven fabric for use as the female component of the fastener of Comparative Example 3.

An embossing roll engraved with the pattern shown in FIG. 12 on the surface was used and a nonwoven fabric for use as the female component of the fastener was produced as in the case of Application Example 1. As shown in FIG. 12, the embossed pattern is a diamond pattern arranged in the MD direction and CD direction similar to the diamond pattern of FIG. 11. However, the diamond pattern utilized in FIG. 12 comprises lines of square dots arranged with a predetermined separation. The embossed section 101 had a distance between nodes in the MD direction, $W_8$=8.5 mm, the distance between nodes in the CD direction, $W_9$=8.0 mm, the width of dots in the line direction $W_{10}$=0.685 mm, the width of dots in the line direction plus the width of the dot distance =1.46 mm and the embossed area ratio was 10%.

The adhesive strength, mechanical strength and thickness of the aforementioned nonwoven fabric for use as the female component for the fastener produced above were measured and evaluated. The results obtained are shown in Table 1 below.

Comparative Example 4

Figure 13:
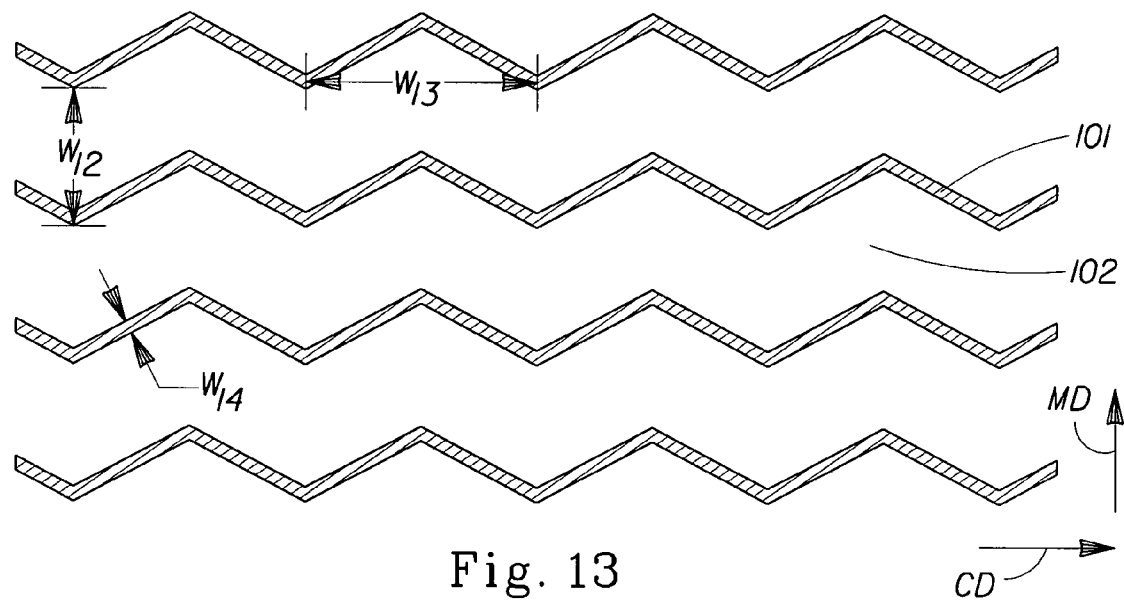
FIG. 13 is a partial top view of the nonwoven fabric for use as the female component of the fastener of Comparative Example 4.

An embossing roll engraved with the pattern shown in FIG. 13 on the surface was used and a nonwoven fabric for use as the female component of the fastener was produced as in the case of Application Example 1. As shown in FIG. 13, the embossed pattern comprised a plurality of unit patterns parallel to the CD direction having a relatively mild zigzag and arranged in the MD direction. The embossed section 101 had the distance between apexes in the MD direction (pitch of the unit pattern) $W_{12}$=7 mm, distance between apexes in the CD direction $W_{13}$=9 mm, line width $W_{14}$=1 mm and embossed area ratio of 16%. Furthermore, the unit pattern adjacent to the MD direction was not contained inside the triangle formed by the adjacent three contact points of the first shaded area and the second shaded area in the aforementioned unit pattern.

Furthermore, the adhesive strength, mechanical strength and thickness of the aforementioned nonwoven fabric for use as the female component for the fastener produced above were measured and evaluated. The results obtained are shown in Table 1 below.

TABLE I

| | | Example Number | | | | |
|---|---|---|---|---|---|---|
| Measured property | Units of measure | Application Example 1 | Comparative Example 1 | Comparative Example 2 | Comparative Example 3 | Comparative Example 4 |
| First propylene type polymer | Wt % | 20 | | 20 | 20 | 20 |
| Second propylene type polymer | Wt % | 80 | 100 | 80 | 80 | 80 |
| Basis weight | gsm | 45 | 45 | 45 | 45 | 45 |

TABLE I-continued

|  | Units of measure | Application Example 1 | Comparative Example 1 | Comparative Example 2 | Comparative Example 3 | Comparative Example 4 |
|---|---|---|---|---|---|---|
| Measured property | | | | | | |
| Embossed area ratio | % | 24 | 24 | 24 | 10 | 16 |
| Embossed pattern | | FIG. 1 | na | FIG. 11 | FIG. 12 | FIG. 13 |
| Peel strength | N | 3.7 | 1.8 | 3.2 | 2.6 | 3 |
| Repeat peel strength | N | 3 | na | 2.7 | 1.1 | 1.4 |
| Tensile shear strength | N | 38 | 14 | 36.9 | 19.3 | 37.2 |
| MD tensile strength | N | 42.3 | 49.2 | 45.8 | 32.6 | 40.5 |
| CD tensile strength | N | 22.7 | 23.4 | 16.1 | 12.8 | 13.9 |
| Thickness | μm | 540 | 380 | 510 | 420 | 550 |

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. A fastening system comprising:
   an engaging component comprising a plurality of engaging elements;
   a receiving component, wherein the engaging component is capable of engaging the receiving member, the receiving component comprising:
      a nonwoven fabric comprising:
         composite fibers having a first propylene polymer and a second propylene polymer, wherein the first and second propylene polymers extend continually in a longitudinal direction and the second propylene type polymer is associated with the first propylene type polymer such that the composite fiber forms a crimp therein;
         embossed sections having a plurality of zigzag unit patterns arranged in a machine direction with predetermined spacings, the zigzag unit patterns continually extending substantially parallel with a cross direction of the embossing roll, wherein the zigzag unit patterns each comprise a continual zigzag pattern in which a plurality of first diagonal lines and a plurality of second diagonal lines are arranged alternately and are connected together adjacent to end parts of the diagonal lines, the first diagonal lines being arranged at a first angle with respect to the cross direction and being inclined to one side at about the same first angle relative to the machine direction, the second diagonal lines being arranged at a second angle with respect to the cross direction and being inclined to the other side at about the same second angle relative to the machine direction, wherein the first diagonal lines and the second diagonal lines in the zigzag unit pattern form triangles comprising three adjacent contact points of diagonal lines, the triangles including part of the zigzag unit pattern extending in the machine direction adjacent thereto; and
      nonembossed sections,
   wherein the composite fibers are bonded together in the embossed sections, and wherein the unit pattern has a ratio of $W_1/W_2$ in the range of about 0.5 to about 2.0.

2. The fastening system of claim 1, wherein the predetermined spacing $W_3$ is between about 2 mm to about 5 mm and $W_1$ is between about 5 mm to about 20 mm.

3. The fastening system of claim 1, wherein at least one of the first diagonal lines extends beyond a contact point.

4. The fastening system of claim 1, wherein at least one of the second diagonal lines extends beyond a contact point.

5. The fastening system of claim 1, wherein the embossed section further comprises dot patterns which are disposed between two adjacent unit patterns and in which the composite fibers are bonded together by thermocompression bonding with an embossing roll.

6. The fastening system of claim 1, wherein the first and second propylene polymers have a ratio of melt flow rate (MFR, 230° C., 2.16 kg load) measured in accordance with ASTM D 1238 in the range of 0.8 to 1.2 (second propylene polymer/first propylene polymer).

7. The fastening system of claim 1, wherein the first and second propylene polymers are each a propylene homopolymer or a propylene/ethylene random copolymer having an ethylene unit content in the range of 0 to 10 mol % and a melt flow rate (MFR, 230° C., 2.16 kg load) in the range of 20 to 200 g/10 min as measured in accordance with ASTM D 1238.

8. The fastening system of claim 1, wherein the nonwoven fabric comprises a laminate wherein the nonwoven fabric comprising the crimped composite fiber is disposed as an outermost layer of the laminate, and wherein at least one layer is laminated on a back surface of the nonwoven fabric.

9. The fastening system of claim 7, wherein the nonwoven fabric comprises a laminate wherein the nonwoven fabric is joined to a second nonwoven fabric comprising a propylene polymer fiber in a face-to-face orientation.

10. A disposable article comprising: an outer-facing surface, a wearer-facing surface, and a fastening system disposed on the outer-facing surface or the wearer-facing surface of the article, the fastening system comprising:

an engaging component comprising a plurality of engaging elements;

a receiving component, wherein the engaging component is capable of engaging the receiving member, the receiving component comprising:

a nonwoven fabric comprising:

composite fibers having a first propylene polymer and a second propylene polymer, wherein the first and second propylene polymers extend continually in a longitudinal direction and the second propylene type polymer is associated with the first propylene type polymer such that the composite fiber forms a crimp therein;

embossed sections having a plurality of zigzag unit patterns arranged in a machine direction with predetermined spacings, the zigzag unit patterns continually extending substantially parallel with a cross direction of the embossing roll, wherein the zigzag unit patterns each comprise a continual zigzag pattern in which a plurality of first diagonal lines and a plurality of second diagonal lines are arranged alternately and are connected together adjacent to end parts of the diagonal lines, the first diagonal lines being arranged at a first angle with respect to the cross direction and being inclined to one side at about the same first angle relative to the machine direction, the second diagonal lines being arranged at a second angle with respect to the cross direction and being inclined to the other side at about the same second angle relative to the machine direction, wherein the first diagonal lines and the second diagonal lines in the zigzag unit pattern form triangles comprising three adjacent contact points of diagonal lines, the triangles including part of the zigzag unit pattern extending in the machine direction adjacent thereto; and nonembossed sections, wherein the composite fibers are bonded together in the embossed sections, and wherein the unit pattern has a ratio of $W_1/W_2$ in the range of about 0.5 to about 2.0.

11. The disposable article of claim 10, wherein the article is selected from group consisting of: an absorbent article, a diaper, a pant, an adult incontinence article, a feminine hygiene article, a body wrap, a bib, and a consumer good.

12. The disposable article of claim 11, wherein the article is a diaper, and wherein the receiving component is joined to an outer-facing surface of the diaper.

13. The disposable article of claim 10, wherein the predetermined spacing $W_3$ is between about 2 mm to about 5 mm and $W_1$ is between about 5 mm to about 20 mm.

14. The disposable article of claim 13, wherein at least one of the first diagonal lines extends beyond a contact point.

15. The disposable article of claim 13, wherein at least one of the second diagonal lines extends beyond a contact point.

16. The disposable article of claim 13, wherein the embossed section further comprises dot patterns which are disposed between two adjacent unit patterns and in which the composite fibers are bonded together by thermocompression bonding with an embossing roll.

17. The disposable article of claim 12 wherein the diaper includes a first waist region, a second waist region, a crotch region disposed between the first and second waist regions; a first waist edge and a second waist edge; and a first longitudinal edge and a second longitudinal edge; wherein the diaper further comprises:

a topsheet;

a backsheet joined to at least a portion of the topsheet; and an absorbent core disposed between the topsheet and the backsheet; and a pair of side panels extending outward from the first and second longitudinal edges in the first waist region of the diaper, wherein the engaging elements are joined to the side panels, and wherein the receiving components are joined to the second waist region.

18. The disposable article of claim 12 wherein the diaper includes a first waist region, a second waist region, a crotch region disposed between the first and second waist regions; a first waist edge and a second waist edge; and a first longitudinal edge and a second longitudinal edge; wherein the diaper further comprises:

a topsheet;

a backsheet joined to at least a portion of the topsheet; and an absorbent core disposed between the topsheet and the backsheet; and a first side panel extending outward from the first longitudinal edge in the first waist region of the diaper, wherein the a first engaging component and a first receiving component are joined to the first side panel; and a second side panel extending outward from the second longitudinal edge in the first waist region of the diaper, wherein a second engaging component and a second receiving component are joined to the first side panel, and wherein the first engaging component is capable of engaging the second receiving component or the second engaging component is capable of engaging the first receiving component.

19. The disposable article of claim 18 further comprising a receiving component joined to the backsheet of the diaper in the second waist region.

\* \* \* \* \*